United States Patent
Chia et al.

(10) Patent No.: US 10,132,810 B2
(45) Date of Patent: Nov. 20, 2018

(54) METHOD FOR ASSESSING AND PREDICTING EFFICACY OF BREAST CANCER TREATMENT WITH A LONG-ACTING TOPOISOMERASE I INHIBITOR

(71) Applicant: Nektar Therapeutics, San Francisco, CA (US)

(72) Inventors: Yen Lin Chia, Los Gatos, CA (US); Ute Hoch, San Francisco, CA (US); Alison Hannah, Sebastopol, CA (US); Michael A. Eldon, Redwood City, CA (US)

(73) Assignee: Nektar Therapeutics, San Francsico, CA (US)

( * ) Notice: Subject to any disclaimer, the term of this patent is extended or adjusted under 35 U.S.C. 154(b) by 0 days.

(21) Appl. No.: 14/648,042

(22) PCT Filed: Nov. 27, 2013

(86) PCT No.: PCT/US2013/072205
§ 371 (c)(1),
(2) Date: May 28, 2015

(87) PCT Pub. No.: WO2014/085571
PCT Pub. Date: Jun. 5, 2014

(65) Prior Publication Data
US 2015/0309032 A1 Oct. 29, 2015

Related U.S. Application Data

(60) Provisional application No. 61/730,900, filed on Nov. 28, 2012.

(51) Int. Cl.
*G01N 33/574* (2006.01)
*A61K 31/4745* (2006.01)
*A61K 47/60* (2017.01)

(52) U.S. Cl.
CPC ... *G01N 33/57415* (2013.01); *A61K 31/4745* (2013.01); *A61K 47/60* (2017.08); *G01N 33/574* (2013.01); *G01N 2333/4725* (2013.01); *G01N 2333/705* (2013.01); *G01N 2800/52* (2013.01)

(58) Field of Classification Search
None
See application file for complete search history.

(56) References Cited

U.S. PATENT DOCUMENTS

| 6,258,540 B1 * | 7/2001 | Lo | C12Q 1/6879 435/440 |
| 6,355,623 B2 * | 3/2002 | Seidman | A61K 31/52 514/263.4 |
| 7,744,861 B2 | 6/2010 | Zhao et al. | |
| 8,263,062 B2 | 9/2012 | Zhao et al. | |
| 8,771,662 B2 | 7/2014 | Zhao et al. | |
| 8,906,353 B2 * | 12/2014 | Eldon | A61K 31/4745 424/78.08 |
| 2002/0103141 A1 * | 8/2002 | McKearn | A61K 31/00 514/43 |
| 2011/0269789 A1 * | 11/2011 | Eldon | A61K 31/4745 514/283 |

FOREIGN PATENT DOCUMENTS

| WO | WO 2007/092646 A2 | 8/2007 |
| WO | WO 2009/059393 A1 | 5/2009 |
| WO | WO 2010/036335 A1 | 4/2010 |
| WO | WO 2011/063156 A2 | 5/2011 |
| WO | WO 2011/127219 A1 | 10/2011 |
| WO | WO 2012/031320 A1 | 3/2012 |
| WO | WO 2013/063286 A1 | 5/2013 |

OTHER PUBLICATIONS

Gion et al. (Euro. J. Cancer 2001, 37: 355-363).*
Thaker, NG (CA 27-29, Medscape Reference Sep. 23, 2012, http://web.archive.org/web/20120923215147/http://emedicine.medscape.com/article/2087535-overview).*
PCT International Search Report and Written Opinion corresponding to PCT Application No. PCT/US2013/072205 dated Apr. 1, 2014.
PCT International Preliminary Report on Patentability corresponding to PCT Application No. PCT/US2013/072205 dated Jun. 11, 2015.
Avril et al., "Response to Therapy in Breast Cancer", J. Nucl. Med., vol. 50, pp. 55S-63S, (2009).
Awada et al., "Two schedules of etirinotecan pegol (NKTR-102) in patients with previously treated metastatic breast cancer: a randomised phase 2 study", www.thelancet.com/oncology, pp. 1-10, Published online Oct. 4, 2013.
Chourb et al., "Improved detection of the MUC1 cancer antigen CA 15-3 by ALYGNSA fluorimmunoassay", SciRes., vol. 3, No. 8, pp. 524-528, (2011).
Coderoni et al., "Phosphorylation Sites for Type N II Protein Kinase in DNA-Topoisomerase I From Calf Thymus", Int. J. Biochem., vol. 22, No. 7, pp. 737-746, (1990).
Delgado et al., "Standardization of Carcinoembryonic Antigen Testing in the Setting of Clinical Laboratory Consolidation", Laboratory Medicine, vol. 32, No. 2, pp. 92-95, (Feb. 2001).

(Continued)

*Primary Examiner* — Peter J Reddig
(74) *Attorney, Agent, or Firm* — Susan T. Evans

(57) ABSTRACT

Provided is a method of treating an individual suffering from a cancer such as breast cancer by administering to the individual a long-acting topoisomerase I inhibitor such as SN-38 or irinotecan, and correlating the level of at least one tumor marker such as CA27.29 in the individual with response of the cancer to treatment with the long-acting topoisomerase I inhibitor, to thereby provide a method for predicting and assessing the therapeutic efficacy of the treatment.

17 Claims, 10 Drawing Sheets

(56) References Cited

OTHER PUBLICATIONS

Eisenhauer et al., "New response evaluation criteria in solid tumours: Revised REGIST guideline (version 1.1)", European Journal of Cancer, vol. 45, pp. 228-247, (2009).

Eldon et al., "Population pharmacokinetics of NKTR-102, a topoisomerase I inhibitor-polymer conjugate, in patients with advanced solid tumors", J. Clin. Oncol., vol. 29, (suppl; abstr 2598), (2011).

Harris et al., "American Society of Clinical Oncology 2007 Update of Recommendations for the Use of Tumor Markers in Breast Cancer", Journal of Clinical Oncology, vol. 25, No. 33, pp. 5287-5312, (Nov. 20, 2007).

Jameson et al., "A Multicenter, Phase I, Dose-Escalation Study to Assess the Safety, Tolerability, and Pharmacokinetics of Etirinotecan Pegol in Patients with Refractory Solid Tumors", Clin. Cancer Res., vol. 19, No. 1, pp. 268-278, (Jan. 1, 2013).

Kaiserman et al., "Regulation of Xenopus laevis DNA Topoisomerase I Activity by Phosphorylation in Vitro", Biochemistry, vol. 27, pp. 3216-3222, (1988).

Kehrer et al., "Factors Involved in Prolongation of the Terminal Disposition Phase of SN-38: Clinical and Experimental Studies", Clinical Cancer Research, vol. 6, pp. 3451-3458, (Sep. 2000).

Patnaik et al., "EZN-2208, a novel anticancer agent, in patients with advanced malignancies: a Phase 1 dose-escalation study", AACR-NCI-EORTC, Boston MA, Poster C221, 1 page, (Nov. 18, 2009).

Persson et al., "Polyethylene glycol conjugation of irinotecan improves its antitumor activity in three mouse xenograft models", AACR-NCI-EORTC Intl. Conference: Molecular Targets and Cancer Therapeutics, Poster No. C10, (Oct. 22-26, 2007).

Pommier et al., "Mechanism of action of eukaryotic DNA topoisomerase I and drugs targeted to the enzyme", Biochimica et Biophysica Acta 1400, pp. 83-106, (1998).

Samuels et al., "DNA Topoisomerase I Phosphorylation in Murine Fibroblasts Treated with 12-O-Tetradecanoylphorbol-13-acetate and in Vitro by Protein Kinase C", The Journal of Biological Chemistry, vol. 267, No. 16, Issue of Jun. 5, pp. 11156-11162, (1992).

Sapra et al., "Marked therapeutic efficacy of a novel poly(ethyleneglycol) conjugated SN38 conjugate in xenograft models of breast and colorectal cancers", Enzon Pharmaceuticals, Abstract #145, (no date).

Sapra et al., "Marked therapeutic efficacy of a novel polyethylene glycol-SN38 conjugate, EZN-2208, in xenograft models of B-cell non-Hodgkin's lymphoma", Haemotologica, vol. 94, No. 10, pp. 1456-1459, (2009).

Therasse et al., "New Guidelines to Evaluate the Response to Treatment in Solid Tumors", Journal of the National Cancer Institute, vol. 92, No. 3, pp. 205-216, (Feb. 2, 2000).

Turman et al., "A Casein Kinase Type II (CKII)-like Nuclear Protein Kinase Associates with, Phosphorylates, and Activates Topoisomerase I", Biochemical Medicine and Metabolic Biology, vol. 50, pp. 210-225, (1993).

Wang, "DNA Topoisomerases", Annu. Rev. Biochem., vol. 65, pp. 635-692, (1996).

Zhao et al., "Novel Prodrugs of SN38 Using Multiarm Poly(ethylene glycol) Linkers" Bioconjugate Chem., vol. 19, pp. 849-859, (2008).

Enzon Pharmaceuticals, Macromolecular Engineering Technologies, 16 pages, (2004).

Nektar™—Transforming Therapeutics, Nektar Molecule Engineering: Polyethylene Glycol and Derivatives for Advanced PEGylation, 24 pages, Catalog—2003, (Jul. 2003).

Nektar™—Transforming Therapeutics, Nektar Advanced PEGylation: Polyethylene Glycol and Derivatives for Advanced PEGylation, 27 pages, Catalog—2004, (Jul. 2004).

Nektar™—Transforming Therapeutics, Nektar Advanced PEGylation: Polyethylene Glycol and Derivatives for Advanced PEGylation, 33 pages, (Catalog 2005—2006).

NOF Corporation, PEG Derivatives, Phospholipid and Drug Delivery Materials for Pharmaceuticals, 46 pages, Catalogue 2003—$1^{st}$, (Jan. 2003).

NOF Corporation, PEG Derivatives, Phospholipid and Drug Delivery Materials for Pharmaceuticals, 27 pages, Catalogue 2003—$2^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

Polypure Products, PEG amines; PEG acids and amino acids; PEG thiols and disulfides; Biotins, 5 pages, (Apr. 2004).

Polypure Products, PEG amines; PEG acids and amino acids; PEG thiols and disulfides; Biotins, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producer and provider of monodisperse discrete PEG™ (dPEG™) derivatives, (Product Catalog), 26 pages, (Updated: Jul. 18, 2005).

Quanta Biodesign, Ltd., Leading innovator, producer and provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

Enomoto et al., "Two cases of postoperative local skin recurrence of breast cancer—successfully treated with chemotherapy of irinotecan hydrochloride (CPT-11)", Gan to Kagaku Ryoho, vol. 32, No. 11, pp. 1782-1785, (Oct. 2005).

Ikeda et al., "Evaluation of irinotecan hydrochloride (CPT-11) and trastuzumab combination therapy as salvage treatment in patients with HER2 overexpressing metastatic breast cancer", Gan to Kagaku Ryoho, vol. 36, No. 5, pp. 773-777, (May 2009).

English translation of Notification of the First Office Action in Chinese Patent Application No. 201380061709.6 dated Mar. 15, 2016.

English translation of Notification of the Second Office Action in Chinese Patent Application No. 201380061709.6 dated Dec. 19, 2016.

Communication in European Patent Application No. 13 802 833.7 dated Jul. 13, 2016.

English translation of Notification of the Third Office Action in corresponding Chinese Patent Application No. 201380061709.6 dated Aug. 16, 2017.

European Communication in corresponding European Patent Application No. 13 802 833.7-1405 dated Mar. 2, 2017.

European Communication in corresponding European Patent Application No. 13 802 833.7-1405 dated Oct. 11, 2017.

English translation of Notice of Reasons for Rejection in corresponding Japanese Patent Application No. 2015-544204 dated Jun. 22, 2017.

\* cited by examiner

METHOD FOR ASSESSING AND PREDICTING EFFICACY OF BREAST CANCER TREATMENT WITH A LONG-ACTING TOPOISOMERASE I INHIBITOR

CROSS REFERENCE TO RELATED APPLICATIONS

This application is a 35 U.S.C. § 371 application of International Application No. PCT/US2013/072205, filed Nov. 27, 2013, designating the United States, which claims the benefit of priority under 35 U.S.C. § 119(e) to U.S. Provisional Patent Application No. 61/730,900 filed Nov. 28, 2012, the disclosures of which are incorporated herein by reference in their entireties.

FIELD OF THE INVENTION

This invention relates to (among other things) the field of cancer chemotherapy. More specifically, the invention involves the treatment of an individual suffering from a cancer such as breast cancer by administering to the individual a long-acting topoisomerase I inhibitor, and correlating the level of one or more tumor markers in the individual with response of the cancer to treatment with the long-acting topoisomerase I inhibitor, to thereby provide a method for predicting and assessing the therapeutic efficacy of the treatment.

BACKGROUND OF THE INVENTION

Topoisomerase I is an enzyme that plays an important and critical role in cellular proliferation. As such, by inhibiting this enzyme, highly proliferative cells are preferentially targeted and unable to propagate. Thus, this enzyme is a highly attractive target for chemotherapeutic agents, especially in human cancers.

Topoisomerase I catalyzes the uncoiling of DNA during replication and transcription. See Pommier et al. (1998), *Biochim. Biophys. Acta.* 1400(1-3):83-105 and Wang (1996), *Annu. Rev. Biochem.,* 65:635-92. The activity of topoisomerase I is regulated by phosphorylation, primarily on serine residues (Turman et al. (1993) *Biochem. Med. Metab. Biol.,* 50(2):210-25; Coderoni et al. (1990), *Int. J. Biochem.* 22(7):737-46; Kaiserman et al. (1988), *Biochemistry,* 27(9):3216-22; Samuels et al. (1992) *J. Biol. Chem.* 267(16):1156-62)], and appears to be necessary for the initial complex formation between the enzyme and DNA (Coderoni et al. (1990), *Int. J. Biochem.* 22(7):737-46).

The first topoisomerase I inhibitors to be identified were the camptothecins. Camptothecin (often abbreviated as "CPT") is a phytotoxic alkaloid first isolated from the wood and bark of *Camptotheca acuminata* (Nyssaceae). The compound has a pentacyclic ring system with an asymmetric center in lactone ring E with a 20 S configuration. The pentacyclic ring system includes a pyrrolo[3,4-b]quinoline (rings A, B and C), a conjugated pyridone (ring D), and a six-membered lactone (ring E) with a 20-hydroxyl group. Due to its insolubility in water, camptothecin was initially evaluated clinically in the form of a water-soluble carboxylate salt having the lactone ring open to form the sodium salt. In an effort to address the poor aqueous solubility associated with camptothecin and many of its derivatives, a number of synthetic efforts have been directed to derivatizing the A-ring and/or B-ring or esterifying the 20-hydroxyl to improve water-solubility while maintaining cytotoxic activity. For example, topotecan (9-dimethylaminomethyl-10-hydroxy CPT), 10-hydroxy-7-ethyl-camptothecin (also known as SN-38, a metabolite resulting from hydrolysis of irinotecan) and irinotecan (7-ethyl-10[4-(1-piperidino)-1-piperidino]carbonyloxy CPT), otherwise known as CPT-11, are water-soluble CPT derivatives that have shown clinically useful activity. Recently, long acting forms of topoisomerase I inhibitors such as the foregoing have been developed. See, e.g., U.S. Pat. Nos. 8,263,062 and 7,744,861, Zhao, H., et al., *Bioconjugate Chem.* 2008, 19, 849-859, and Sapra, P., et al., *Haematologica,* 2009; 94(10), 1456-1459. Such long acting topoisomerase I inhibitors have been shown to be efficacious against a range of human xenograft tumors including breast cancer (Persson, H., et al., AACR-NCI-EORTC Intl Conference on Molecular Targets and Cancer Therapeutics, Oct. 22-26, 2007, S. F. CA. Poster No. C10).

Increasing numbers of patients with diagnosed breast cancer receive primary systemic therapy followed by surgery. In certain cancers such as breast cancer, monitoring a patient's response to treatment is an essential component of therapy, since the degree of response can provide important prognostic information related to disease-free and overall survival. Histopathology provides an accurate assessment of treatment efficacy on the basis of the extent of residual tumor and regressive changes within the tumor tissue. However, only 20% of breast cancer patients achieve a pathologic complete response, a fact that necessitates methods for monitoring therapeutic effectiveness early during therapy (Avril, N. et al., *The Journal of Nuclear Medicine,* 50 (5) Suppl., May 2009, 55S-63S). Early identification of ineffective therapy may also be useful in patients with metastatic breast cancer due to the number of palliative treatment options. Commonly used methods for assessing efficacy early in treatment include MRI (magnetic resonance imaging), which is expensive and requires both highly specialized equipment and highly trained experts, and radiation-based methods such as CT (computerized axial tomography) scans. New and improved methods for predicting therapeutic effectiveness during treatment of breast cancer, especially those that are efficient, convenient, and cost-effective, could help individualize and customize treatment, and to avoid ineffective chemotherapies.

Thus, there remains a need to provide (among other things) methods for assessing and predicting the efficacy of breast cancer treatment regimens, in particular in patients undergoing therapy with a long-acting topoisomerase-I inhibitor.

The present invention seeks to address these and other needs in the art.

SUMMARY OF THE INVENTION

In one aspect, the present invention is directed to a method for assessing response to treatment with a long-acting topoisomerase-I inhibitor.

More specifically, provided herein is a method for assessing response to treatment with a long-acting topoisomerase-I inhibitor in a subject diagnosed with breast cancer, where the method comprises the following steps: (i) determining the level of a tumor marker in a bodily fluid sample of the subject to provide a reference level of the tumor marker, where the tumor marker is selected from, for example, CA27.29, CA15-3, and carcinoembryonic antigen (CEA), (ii) treating the subject over a duration of time of at least 2 weeks by administering a dosage amount of the long-acting topoisomerase inhibitor on a given dosing schedule, (iii) determining the level of the tumor marker in a bodily fluid sample of the subject following the treating in step (ii), wherein the bodily fluid is the same as in step (i), (iv) correlating the level of the tumor marker in step (iii) with response of the breast cancer to treatment with the long-acting topoisomerase I inhibitor, wherein in the event of a level of the tumor marker in step (iii) that is either unchanged or reduced from the reference level in step (i), a positive response to treatment is determined, and in the event of a level of tumor marker in step (iii) that is increased from the reference level in step (i), a negative response to treatment is determined.

In a particular embodiment, the tumor marker is CA27.29.

In a further embodiment related to the foregoing method and related embodiments, exposure of the breast cancer to SN-38 resulting from the treating step correlates with the level of the tumor marker in the subject and the efficacy of the treatment regimen.

According to yet another aspect, the invention is directed to use of the level of a tumor marker selected from, for example, CA27.29, CA15-3, and CEA, in a bodily fluid selected from blood, serum, and plasma, for predicting efficacy of treatment with a long-acting topoisomerase-I inhibitor such as long-acting irinotecan and long-acting SN-38 in a subject diagnosed with breast cancer.

In yet a further aspect, provided herein is the use of the level of a tumor marker selected from, for example, CA27.29, CA15-3, and CEA, in a bodily fluid selected from blood, serum, and plasma, for predicting exposure of breast cancer to levels of SN-38 resulting from treatment of the breast cancer with a long-acting topoisomerase-I inhibitor such as long-acting irinotecan and long-acting SN-38 in a subject diagnosed with breast cancer, and exposure of the breast cancer to SN-38 correlates with efficacy of treatment.

In one embodiment related to the foregoing method and uses, the tumor marker is used alone for determining response of the breast cancer to treatment with the long-acting topoisomerase I inhibitor.

In one embodiment related to the method for assessing response to treatment with a long-acting topoisomerase-I inhibitor in a subject diagnosed with breast cancer, the reference level of the tumor marker in step (i) is elevated over normal baseline levels. In one or more related embodiments, the tumor marker is CA27.29 and the reference level of CA27.29 is greater than 38 U/mL. In yet another one or more embodiments, the tumor marker is CA15-3 and the reference level of CA15-3 is greater than 30 U/ml. In yet an additional embodiment, the tumor marker is CEA, and the reference level of CEA is greater than about 4 ng/ml.

In yet another embodiment related to the foregoing method, the duration of treatment is selected from one of the following: at least 3 weeks; at least 6 weeks, and at least 12 weeks.

In yet a further embodiment, the level of the tumor marker is determined by an immunoassay.

In yet a further embodiment of the method, a reduction in the level of the tumor marker of at least 25% by week 6 shows a positive correlation with progression-free survival in the subject of at least 4 months.

In yet an additional embodiment of the method, step (iii) is optionally repeated, either following additional treatment with the long-acting topoisomerase inhibitor I or following the cessation of treatment.

In yet an additional embodiment of the method, in the event of determining a negative response to treatment in step (iv), either the dosage amount or dosing schedule in step (ii) or both are altered.

In an additional embodiment related to the foregoing aspects and uses of the invention, and related embodiments, the subject has metastatic breast cancer.

In yet a further embodiment related to the foregoing aspects and uses of the invention and related embodiments, the subject has failed to respond to prior chemotherapeutic treatment for the breast cancer. In one embodiment related to the foregoing, the subject has failed to respond to prior chemotherapeutic treatment with a taxane such as docetaxel or paclitaxel. In yet another embodiment related to the foregoing, the subject has failed to respond to prior chemotherapeutic treatment with a platinum-based chemotherapeutic agent such as cisplatin.

In one or more embodiments related to the foregoing method and uses, the long-acting topoisomerase-I inhibitor comprises a topoisomerase-I inhibitor compound that is modified by releasable covalent attachment to one or more water-soluble polymers. Exemplary long-acting topoisomerase-I inhibitor compounds include SN-38 modified by releasable covalent attachment to one or more water-soluble polymers and irinotecan modified by releasable covalent attachment to one or more water-soluble polymers.

In one or more additional embodiments related to the foregoing method and uses, the one or more water-soluble polymers attached to the topoisomerase-I inhibitor are selected from poly(alkylene glycol), poly(olefinic alcohol), poly(vinylpyrrolidone), poly(hydroxyalkylmethacrylamide), poly(hydroxyalkylmethacrylate), poly(saccharide), poly(α-hydroxy acid), poly(acrylic acid), poly(vinyl alcohol), polyphosphazene, polyoxazoline, poly(N-acryloylmorpholine), or copolymers or terpolymers thereof. In a preferred embodiment, the water-soluble polymer is a poly(ethylene glycol).

Illustrative long-acting topoisomerase-I inhibitor compounds for use in the method include pentaerythritolyl-4-arm-(polyethyleneglycol-1-methylene-2 oxo-vinylamino acetate-linked-irinotecan) and tetrakis[(4S)-4,11-diethyl-9-hydroxy-3,14-dioxo-3,4,12,14-tetrahydro-1H-pyrano[3',4': 6,7]indolizino[1,2-b]quinolin-4-yl]N,N',N'',N'''-({α,α',α'', α'''-[oxybis(propane-3,1,2-triyl)]tetrakis[poly (oxyethylene)]}tetrakis[oxy(1-oxoethylene)])tetraglycinate. In addition, mixed salts (such as a TFA-HCl mixed salt) and hydrohalic salts (e.g., hydrochloric salts) of the foregoing can be used.

In yet a further embodiment of the method and related embodiments, in step (i), the level of the tumor marker is determined prior to treatment with the long-acting topoisomerase-I inhibitor.

In yet an additional embodiment related to any one or more of the foregoing aspects or embodiments, the bodily fluid sample in steps (i) and (iii) is selected from plasma, serum, and blood.

Each of the herein-described features of the invention is meant to apply equally to each and every embodiment as described herein, unless otherwise indicated.

Additional embodiments of the invention are set forth in the following description and claims.

BRIEF DESCRIPTION OF THE DRAWINGS

FIG. 4A corresponds to patients with RECIST CR or PR (n=15); FIG. 4B corresponds to patients with RECIST SD of greater than or equal to 6 months (n=5); FIG. 4C corresponds to patients with RECIST SD of less than 6 month (n=11); and FIG. 4D corresponds to patients with RECIST PD (n=10).

DETAILED DESCRIPTION OF THE INVENTION

Definitions

Figure 1A:
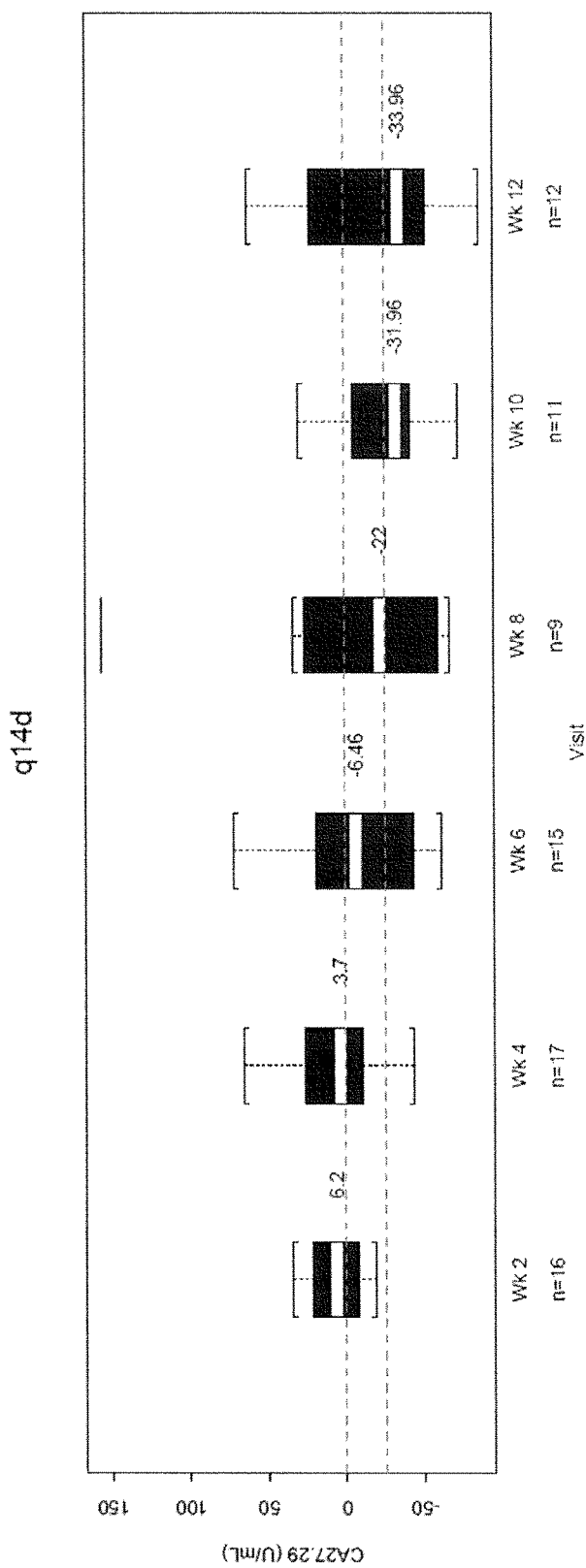
FIGS. 1A and 1B show the change (%) in serum CA27.29 profiles after administration of 145 mg/m$^2$ 4-arm-PEG-gly-irino-20K q14d (FIG. 1A) or q21d (FIG. 1B), where n equals the number of CA27.29 evaluable samples available after each cycle, as described in Example 2.

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic polymer" refers to a polymer that is at least 35% (by weight) soluble, preferably greater than 70% (by weight), and more preferably greater than 95% (by weight) soluble, in water at room temperature. Typically, an unfiltered aqueous preparation of a "water-soluble" polymer transmits at least 75%, more preferably at least 95%, of the amount of light transmitted by the same solution after filtering. It is most preferred, however, that the water-soluble polymer is at least 95% (by weight) soluble in water or completely soluble in water. With respect to being "non-peptidic," a polymer is non-peptidic when it has less than 35% (by weight) of amino acid residues.

The terms "monomer," "monomeric subunit" and "monomeric unit" are used interchangeably herein and refer to one of the basic structural units of a polymer. In the case of a homo-polymer, a single repeating structural unit forms the polymer. In the case of a co-polymer, two or more structural units are repeated—either in a pattern or randomly—to form the polymer. Preferred polymers used in connection with the present invention are homo-polymers. The water-soluble, non-peptidic polymer comprises one or more monomers serially attached to form a chain of monomers.

"PEG" or "polyethylene glycol," as used herein, is meant to encompass any water-soluble poly(ethylene oxide). Unless otherwise indicated, a "PEG polymer" or a polyethylene glycol is one in which substantially all (preferably all) monomeric subunits are ethylene oxide subunits, though, the polymer may contain distinct end capping moieties or functional groups, e.g., for conjugation. PEG polymers for use in the present invention will comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. As stated above, for the PEG polymers, the variable (n) ranges from about 3 to 4000, and the terminal groups and architecture of the overall PEG can vary.

"Branched," in reference to the geometry or overall structure of a polymer, refers to a polymer having two or more polymer "arms" extending from a branch point.

A "physiologically cleavable" or "hydrolyzable" or "degradable" or "releasable" bond is a relatively labile bond that reacts with water (i.e., is hydrolyzed) under physiological conditions. The tendency of a bond to hydrolyze in water may depend not only on the general type of linkage connecting two atoms within a given molecule but also on the substituents attached to these atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Pharmaceutically acceptable excipient" or "pharmaceutically acceptable carrier" refers to a component that may be included in the compositions of the invention causes no significant adverse toxicological effects to a patient.

The term "patient," refers to a living organism suffering from or prone to a condition that can be prevented or treated by administration of a compound of the invention as described herein, and includes both humans and animals.

Overview

As indicated above, the present invention is directed to (among other things) the treatment of an individual suffering from a cancer such as breast cancer by administering to the individual a long-acting topoisomerase I inhibitor, and correlating the level of one or more tumor markers in the individual with response of the cancer to treatment with the long-acting topoisomerase I inhibitor, to thereby provide a method for predicting and assessing the therapeutic efficacy of the treatment.

Tumor markers are substances that are associated with a malignancy. They are either produced by tumor-cells (tumor-derived) or by the body in response to tumor cells (tumor-associated). They are typically substances that are released into the circulation and thus can be measured. In 2007, the American Society of Clinical Oncology (ASCO) published updated recommendations for the use of tumor markers in the prevention, screening, treatment and surveillance of breast cancer. The update was based upon the review and analysis of data published since 1999 (Harris L, et al., *J Clin Oncol* 2007, 25:5287-5312).

Two biomarkers that are highly associated with breast cancer are cancer antigens 15-3 and 27.29, commonly referred to as CA15.3 and CA27-29. Both are derived from the MUC1 gene. Based upon the updated recommendations published by ASCO in 2007, present data (i) are insufficient to recommend either CA15.3 or CA27-29 for screening, diagnosis and staging, (ii) do not support the use of CA15.3 or CA27-29 for monitoring patients for recurrence after primary breast cancer therapy, and (iii) are insufficient to recommend the use of CA15.3 or CA27.29 alone for monitoring response to treatment. In conjunction with diagnostic imaging, history, and physical examination, these tumor markers may be used to monitor patients with metastatic disease during active therapy. Similar recommendations are provided by ASCO (2007) regarding the tumor marker CEA in breast cancer.

Figure 1B:
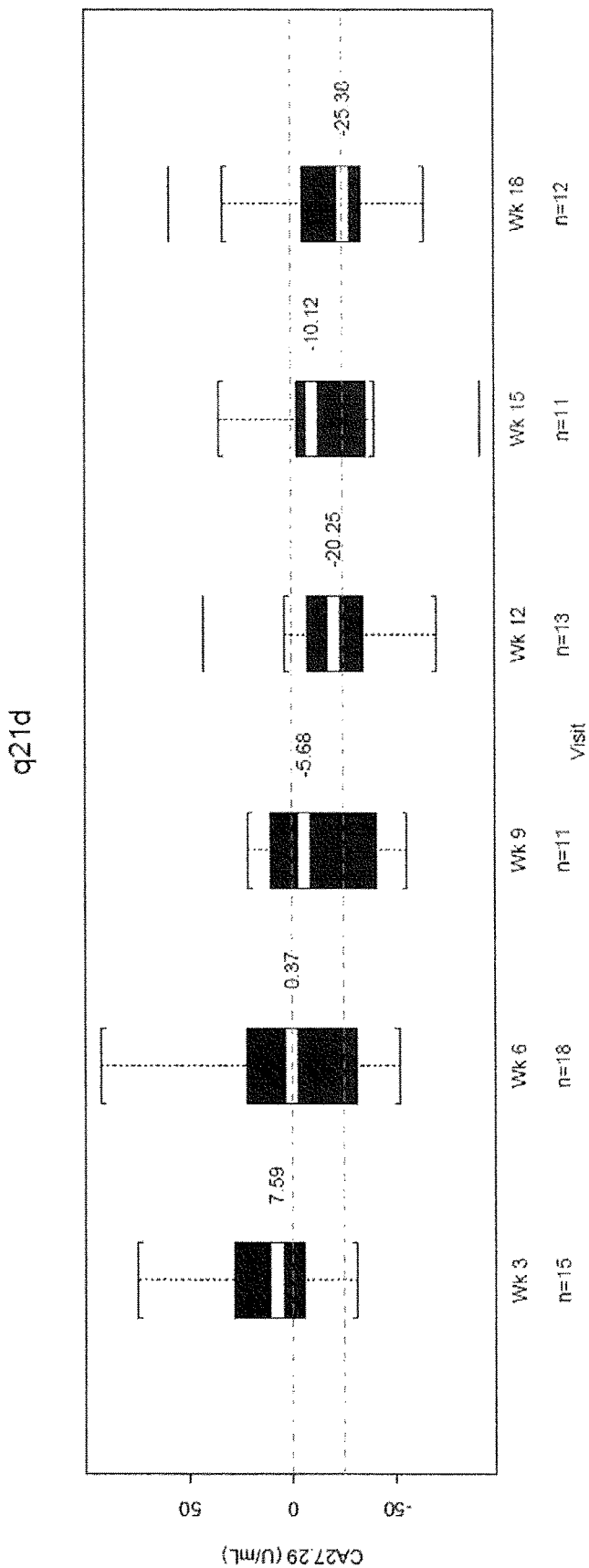

Despite the foregoing recommendations against the use of the tumor markers CA15.3 and CA27.29 for screening, diagnosis, staging, and monitoring for recurrence after primary therapy, and in keeping with the ASCO Guidelines (2007) which state that such tumor markers can be used to monitor patients with metastatic disease during active therapy in conjunction with other detection methods, an unexpected and surprising trend in serum CA27.29 levels over the course of treatment with a long-acting topoisomerase-I inhibitor in patients diagnosed with breast cancer was observed, see, e.g., FIGS. 1A and 1B, and led to the development of a mathematical model linking the kinetics of the MUC-1 antigen to SN-38 exposure, tumor size and RECIST (response evaluation criteria in solid tumors), to thereby provide a method for predicting response to treatment with the long-acting topoisomerase-I inhibitor under various clinical scenarios. While in no way intending to be bound by theory, it is believed that the long-acting nature of the topoisomerase-I inhibitor, by virtue of its ability to improve the pharmacokinetics of the active metabolite, SN-38, whereby the solid tumor is provided sustained exposure to SN-38 throughout the dosing interval, contributes to the observed correlation of MUC-1 tumor marker concentration to SN-38 exposure.

Method

The method described herein involves the administration of a long acting topoisomerase I inhibitor. In this regard, the invention is not limited to any specific topoisomerase I inhibitor so long as the topoisomerase I inhibitor is long-acting. A topoisomerase I inhibitor is long acting when the effective half-life of the topoisomerase inhibitor satisfies one or more of the following ranges: is from about 5 days to about 60 days; from about 9 days to about 60 days; from about 13 days to about 60 days; from about 21 days to about 60 days; from about 28 days to about 60 days; from about 35 days to about 60 days; from about 42 days to about 60; and from about 49 days to about 60 days. Exemplary long-acting topoisomerase-I inhibitor compounds for use in the method include long-acting forms of camptothecin, camptothecin derivatives and metabolites such as camptothecin, topotecan, irinotecan, SN-38, 10-hydroxycamptothecin, and 11-hydroxycamptothecin.

With regard to the effective half life of a drug such as a topoisomerase-I inhibitor, some topoisomerase I inhibitors metabolize into SN-38, which can be primarily responsible for the inhibitory activity of topoisomerase I. As such, those topoisomerase I inhibitors that metabolize into SN-38 often describe their half-lives in terms of the elimination of SN-38 (rather than on the elimination of the topoisomerase I inhibitor itself). Thus, as used herein, the "effective" half-life of a topoisomerase I inhibitor drug is the half-life of the entity—whether the originally administered drug or a metabolite of the originally administered drug—most responsible for the inhibitory activity of topoisomerase I. By way of example, the literature reports the effective half-life of irinotecan (based on the elimination of SN-38) is about two days, while the effective half-life (again, based on the elimination of SN-38) of a topoisomerase-inhibitor polymer conjugate is about fifty days. See, e.g., Kehrer et al. (2000) *Clin. Can. Res.,* 6:3451-3458 and Jameson et al. (2013) *Clin. Can. Res.,* 19:268-278, respectively.

Exemplary and non-limiting examples of long-acting topoisomerase I inhibitors include compounds encompassed by the following formula:

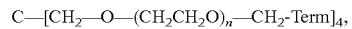

wherein n, in each instance, is an integer having a value from 5 to 150 (e.g., about 113); and Term, in each instance, is selected from the group consisting of —OH, —C(O)OH,

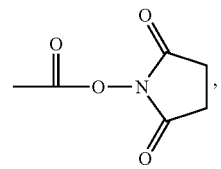

and —NH—CH$_2$—C(O)—O—Irino, wherein Irino is a residue of irinotecan, and, in a composition of such compounds, at least 90% are Irino and the remaining 10% are selected from the group consisting of —OH, —C(O)OH,

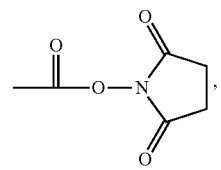

and pharmaceutically acceptable salts (included mixed salts) thereof. Preferably, the irinotecan is modified at its 10-, 11- or 20-ring position. These and other compounds and compositions are described in International Patent Publication No. WO 2011/063156.

Additional exemplary and non-limiting examples of long-acting topoisomerase I inhibitors include compounds encompassed by the following formula:

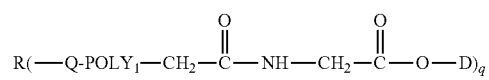

where R is an organic radical possessing from 3 to 150 carbon atoms, Q is a linker, wherein R, when taken together with Q to form R(-Q-)$_q$, is a residue of a polyol or a polythiol after removal of "q" hydroxyl or thiol protons, respectively to form a point of attachment for POLY$_1$; POLY$_1$ is a water-soluble, non-peptidic polymer selected from the group consisting of poly(alkylene glycol), poly(olefinic alcohol), poly(vinylpyrrolidone), poly(hydroxyalkyl-methacrylamide), poly(hydroxyalkyl-methacrylate), poly(α-hydroxy acid), poly(acrylic acid), poly(vinyl alcohol), polyphosphazene, polyoxazoline, poly(N-acryloylmorpholine), and copolymers or terpolymers thereof, D is a camptothecin attached at its 10-, 11- or 20-ring position, and q has a value from 3 to 50, and pharmaceutically acceptable salts (included mixed salts) thereof.

For example, the following pentaerythritol-based multi-arm structures are exemplary and non-limiting compounds that are long-acting topoisomerase I inhibitors:

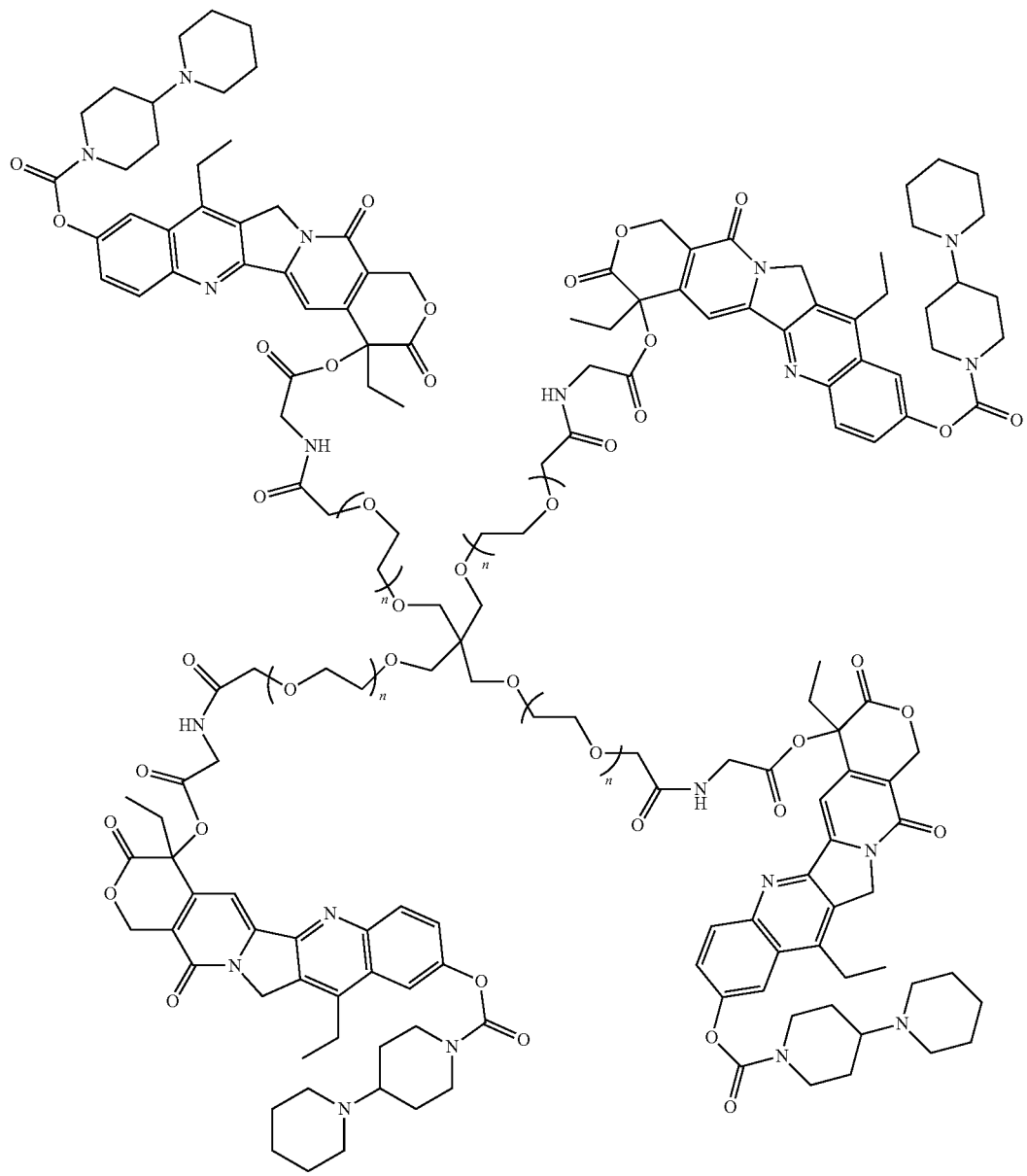

wherein each n is an integer ranging from 40 to about 500 (e.g., about 113 and about 226), and pharmaceutically acceptable salts (included mixed salts) thereof. The above and other compounds are described in U.S. Pat. No. 7,744,861, and are considered "pentaerythritol-based multi-arm polymer conjugates of irinotecan" or a "PBMAPCI."

Further additional exemplary and non-limiting examples of long acting topoisomerase I inhibitors include compounds encompassed by the following formula

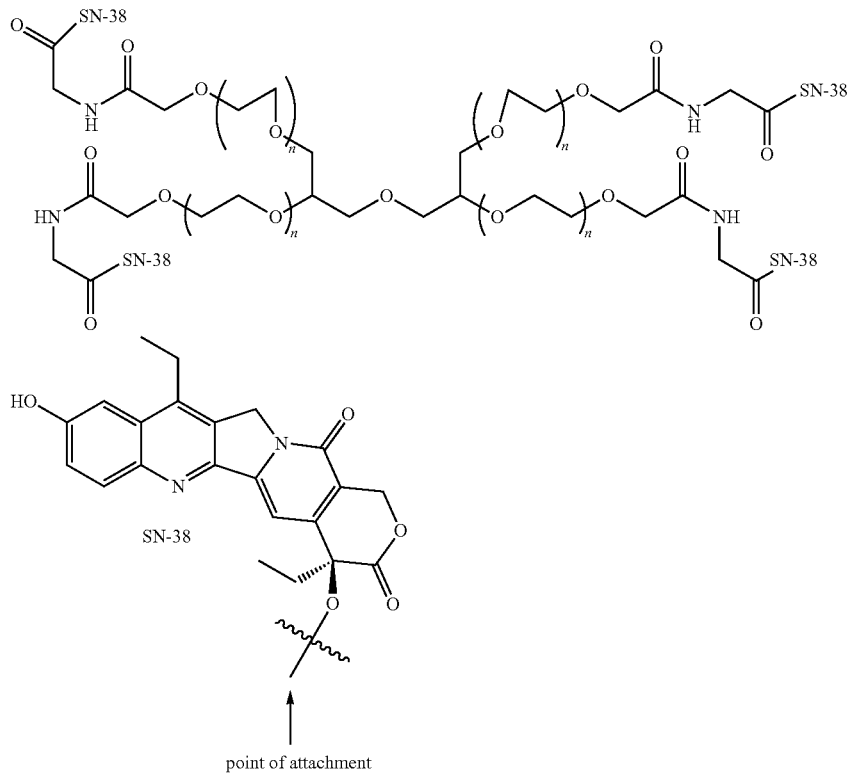

point of attachment wherein each (n) is a positive integer from about 28 to about 341 and each SN-38 is a residue of SN-38. These and other compounds are described in WO 2007/092646, Sapra et al. Abstract 145 entitled "Marked therapeutic efficacy of a novel poly(ethylene-glycol) conjugated SN38 conjugate in xenograft models of breast and colorectal cancers," Patnaik et al. (2009) Poster C221 presented at AACR-NCI-EORTC. In a particular embodiment related to the herein described method and uses, the long-acting topoisomerase inhibitor-I compound is firtecan pegol (also known as EZN-2208 or tetrakis[(4S)-4,11-diethyl-9-hydroxy-3,14-dioxo-3,4,12,14-tetrahydro-1H-pyrano[3',4':6,7]indolizino[1,2-b]quinolin-4-yl]N,N',N'',N'''-({α,α',α'',α'''-[oxybis(propane-3,1,2-triyl)]tetrakis[poly(oxyethylene)]}tetrakis[oxy(1-oxoethylene)]) hetraglycinate).

Additional exemplary and non-limiting examples of long acting topoisomerase I inhibitors include topoisomerase-I inhibitor compounds such as irinotecan, topotecan, camptothecin, or SN-38, modified by releasable covalent attachment to one or more water-soluble polymers such as poly(alkylene glycol), poly(olefinic alcohol), poly(vinylpyrrolidone), poly(hydroxyalkylmethacrylamide), poly(hydroxyalkylmethacrylate), poly(saccharide), poly(α-hydroxy acid), poly(acrylic acid), poly(vinyl alcohol), polyphosphazene, polyoxazoline, poly(N-acryloylmorpholine), or copolymers or terpolymers thereof. Preferably, the water-soluble polymer is a poly(ethylene glycol). Illustrative releasable linkages for releasable covalent attachment of the water-soluble polymer to the topoisomerase-1 inhibitor include carboxylate ester, phosphate ester, anhydrides, acetals, ketals, acyloxyalkyl ether, imines, orthoesters, peptides and oligonucleotides.

Assays for determining whether a given compound can act as a long-acting topoisomerase I inhibitor can be determined through routine pharmacokinetic experimentation by one of ordinary skill in the art.

In accordance with the method described herein, the level of a MUC-1 antigen tumor marker such as CA15-3 or CA27.29 is first determined to provide a baseline or reference value prior to treatment with the long-acting topoisomerase I inhibitor compound. Levels of the tumor marker can be determined in a bodily fluid such as blood, serum, plasma or urine. Preferably, the level is determined in blood, plasma or serum. Generally, CA15-3 is quantified with monoclonal antibodies using either a radioimmunoassay based on a competitive binding principle or using a sandwich format with the ELISA method. ELISA test kits for detecting CA15-3 are available from GenWay Biotech Inc. and Panomics.

The CA15-3 ELISA test is based on the principle of a solid phase enzyme-linked immunosorbent assay. The assay system utilizes a monoclonal antibody directed against a distinct antigenic determinant on the intact CA15-3 molecule and is used for solid phase immobilization (on the microtiter wells). A rabbit anti-CA15-3 antibody conjugated to horseradish peroxidase (HRP) is in the antibody-enzyme conjugate solution. The test sample is allowed to react sequentially with the two antibodies, resulting in the CA15-3 molecules being sandwiched between the solid phase and enzyme-linked antibodies. After two separate 1-hour incubation steps at 37° C., the wells are washed with wash buffer to remove unbound labeled antibodies. A solution of TMB Reagent (3,3',5,5' tetramethyl-benzidine) is added and incubated for 20 minutes, resulting in the development of a blue color. The color development is stopped with the addition of Stop Solution changing the color to yellow. The concentration of CA15-3 is directly proportional to the color intensity of the test sample. Absorbance is measured spectrophotometrically at 450 nm.

Detection of CA15.3 may also be determined using ALYGNSA fluorimmunoassy as described by Chourb. S., et al. SciRes., 3 (8), 524-528 (2011).

Normal levels of CA15-3 are considered to be less than 25 U/ml, therefore, the reference level of CA15-3 prior to commencement of treatment with the long-acting topoisomerase I inhibitor compound will generally be greater than 25 U/ml in patients diagnosed with breast cancer, and more typically will generally be greater than 30 U/ml.

Similarly, an ELISA test kit for detection of CA27.29 is available from Antibodies-Online.com. The kit consists of a microtiter plate pre-coated with an antibody specific to CA27.29. A standard or sample is added to the appropriate microtiter plate well with a biotin-conjugated polyclonal antibody preparation specific for CA27.29. Avidin conjugated to horseradish peroxidase (HRP) is added to each microplate well and incubated. A TMB (3,3',5,5' tetramethyl-benzidine) substrate solution is then added to each well, where only those wells that contain CA27.29, biotin-conjugated antibody and enzyme-conjugated avidin exhibit a change in color. The enzyme-substrate reaction is terminated by the addition of a sulphuric acid solution and the color change is measured spectrophotometrically at a wavelength of 450 nm±2 nm. The concentration of CA27.29 in the samples is then determined by comparing the O.D. of the samples to the standard curve.

Normal levels of CA27.29 are considered to be less than 38 U/ml, therefore, the reference level of CA27.29 prior to commencement of treatment with the long-acting topoisomerase I inhibitor compound will generally be greater than 38 U/ml in patients diagnosed with breast cancer.

In accordance with the method described herein, the level of a tumor marker such as CEA may also be used. The level of CEA is first determined to provide a baseline or reference value prior to treatment with the long-acting topoisomerase I inhibitor. CEA is a 180-kilodalton oncofetal glycoprotein present in the gastrointestinal tract and body fluids of the embryo and fetus. Small amounts of CEA are present in the blood of adults. Normal CEA concentrations of less than 2.5 ng/ml are seen in about 97% of healthy individuals. For use in the present method, the reference of CEA in a patient diagnosed with breast cancer will generally be 4 ng/ml or greater. Detection of CEA is typically conducted by an immunochemiluminometric assay. A description of CEA testing in a clinical setting is provided, e.g., in Delgado, J., et al., Laboratory Medicine (2001). No. 2, 32, 92-95. Levels of the tumor marker can be determined in a bodily fluid, such as blood, serum, plasma or urine. Preferably, the level is determined in blood, plasma or serum.

In accordance with the method described herein, the long-acting topoisomerase I inhibitor is administered to a patient on a given dosing schedule over a time course of at least 2 weeks. Preferably, the long-acting topoisomerase I inhibitor is administered to a patient in a topoisomerase I-inhibiting (i.e., therapeutically effective) amount. One of ordinary skill in the art can determine the dosage of a given topoisomerase I inhibitor sufficient to provide clinically relevant inhibition of topoisomerase I. For example, one of ordinary skill in the art can refer to the literature and/or administer a series of increasing dosages of the topoisomerase inhibitor and determine which amount or amounts provide clinically relevant inhibition of topoisomerase I.

In one or more instances, however, the topoisomerase I-inhibiting amount (particularly with respect to a pentaerythritol-based multi-arm polymer conjugate of irinotecan) is an amount encompassed by one or more of the following ranges: from about 1 mg/m$^2$ to about 1000 mg/m$^2$ of body surface; from about 2 mg/m$^2$ to about 900 mg/m$^2$ of body surface; from about 3 mg/m$^2$ to about 800 mg/m$^2$ of body surface; from about 4 mg/m$^2$ to about 700 mg/m$^2$ of body surface; from about 5 mg/m$^2$ to about 600 mg/m$^2$ of body surface; from about 6 mg/m$^2$ to about 550 mg/m$^2$ of body surface; from about 7 mg/m$^2$ to about 500 mg/m$^2$ of body surface; from about 8 mg/m$^2$ to about 450 mg/m$^2$ of body surface; from about 9 mg/m$^2$ to about 400 mg/m$^2$ of body surface; from about 10 mg/m$^2$ to about 350 mg/m$^2$ of body surface; from about 20 mg/m$^2$ to about 200 mg/m$^2$ of body surface; from about 30 mg/m$^2$ to about 200 mg/m$^2$ of body surface; from about 40 mg/m$^2$ to about 270 mg/m$^2$ of body surface; and from about 50 mg/m$^2$ to about 240 mg/m$^2$ of body surface.

The actual dose to be administered will vary depend upon the age, weight, and general condition of the subject as well as the severity of the condition being treated, the judgment of the health care professional, and particular long-acting topoisomerase I inhibitor compound being administered, particularly in view of its related toxicity.

The unit dosage of any given long-acting topoisomerase I inhibitor can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. For instance, the dosing schedule may include administration every 7 days, every 10 days, every 14 days, every 21 days, and so forth. Once the clinical endpoint has been achieved, dosing of the composition is halted. See, e.g., Example 1, which describes an illustrative dosage amount and dosing schedules for a pentaerythritol-based multi-arm polymer conjugate of irinotecan administered to patients having breast cancer. As can be seen, in Example 1, patients were administered 145 mg/m$^2$ every 14 days (q14d) or every 21 days (q21d). As can be seen in Table 1, both dosing schedules resulted in favorable efficacy and tolerability amongst the patient population.

Typically, the duration of treatment by administration of the long-acting topoisomerase I inhibitor compound, preferably a polymer-modified irinotecan or SN-38, and even more favorably, a multi-arm polymer modified irinotecan or SN-38, i.e., a multi-arm poly(ethylene glycol) irinotecan or SN-38 compound having on average from 3.5-4 topoisomerase-I inhibitor molecules attached to the multi-arm poly(ethylene glycol) core via an amino acid, e.g., glycine, linker, is at least 2 weeks, at least 3 weeks, at least 6 weeks, at least 8 weeks, at least 12 weeks, at least 16 weeks, and so forth.

Following administration of at least one dose of the long-acting topoisomerase I inhibitor compound, the level of the tumor marker in a bodily fluid sample, such as blood, plasma, or serum, is determined (i.e., post-dose level). Generally, the level of the tumor marker determined post-dosing is determined using the same bodily fluid as used for the reference sample taken prior to treatment. Generally, determination of the post-treatment tumor marker level is carried out 1 week after administering the initial dose of the long acting topoisomerase I inhibitor compound, or 10 days after administration of the initial dose, or two weeks after administration of the initial dose, or three weeks after administration of the initial dose, and so forth. However, the level of the tumor-marker post-initial dose can be determined at any day following the initial dosing, although it is preferred to take the first post-dosing tumor marker level at least 3-14 days following administration of the initial dose (e.g., 3, 4, 5, 6,7, 8, 9, 10, 11, 12, 13, or 14 days), due to the long-acting nature of the long-acting topoisomerase-I inhibitor compound, to allow the compound sufficient time to exert a therapeutic and measurable effect on the tumor marker. Over the course of treatment, one or more additional tumor marker determinations can be carried out. For example, tumor marker levels can be determined at 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks and/or 16 weeks following administration of the initial dose, and so forth, or at any combination of time points set forth above.

See, e.g., FIGS. 1A and 1B which show the percent change in serum CA27.29 levels at various time points over the course of treatment. As can be seen, the levels of CA27.29 noticeably decreased over time for both exemplary treatment regimens, in both cases by at least twenty five percent.

As can be seen, the decrease in MUC-1 antigen biomarker CA27.29 from baseline or reference levels over the course of treatment correlates with response of the breast cancer to treatment with the long-acting topoisomerase-I inhibitor compound. See, e.g. Example 3 and FIG. 5.

Figure 2B:
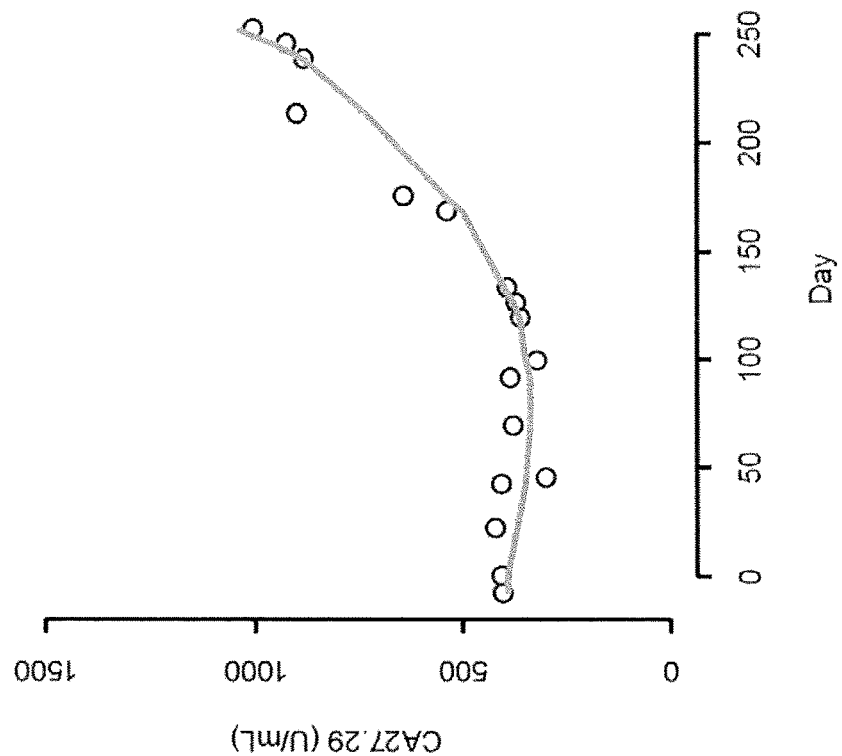
FIGS. 2A, 2B, and 2C are examples of typical CA27.29 profiles over time for individual patients treated as described in Example 1, where the observed values correspond to the circles and the individual predicted CA27.29 levels correspond to the solid lines.
Figure 2A:
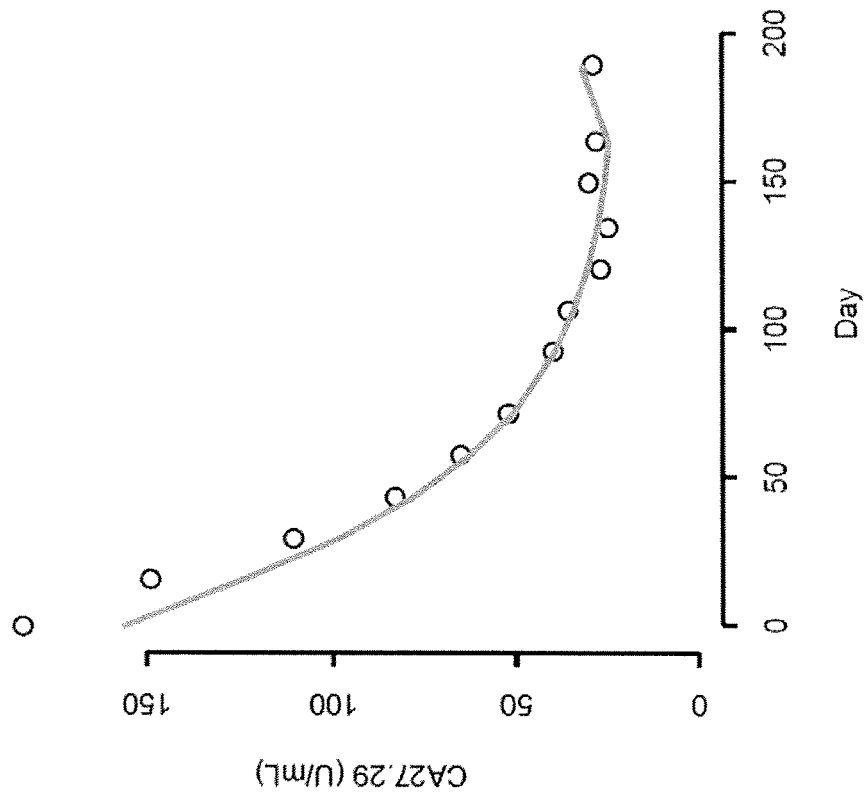
Figure 2C:
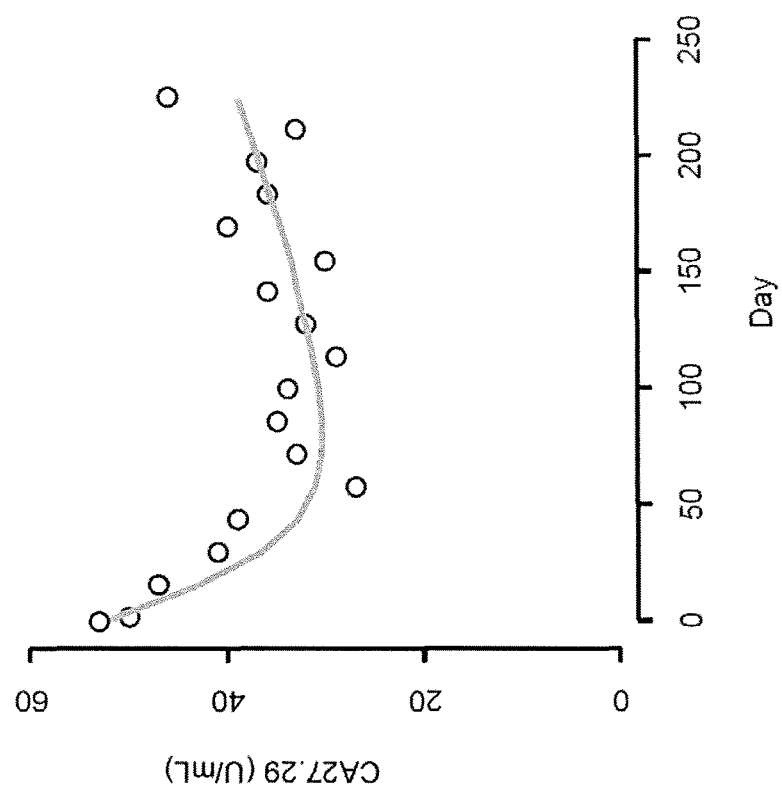

As described in detail in Example 3, based upon the correlation noted above, a model was devised to predict a plasma SN-38 concentration time profile for each patient, to investigate the relationship between predicted SN-38 plasma concentrations and serum CA27.29 levels, to determine whether the metabolite resulting from administration of the long-acting topoisomerase-I inhibitor, SN-38, indirectly inhibits production of CA27.29. The long-acting topoisomerase-I inhibitor compounds utilized in the instant method, such as the pentaerythritol-based multi-arm polymer conjugates of irinotecan described herein, as well as the multi-arm polymer conjugates of SN-38, generally provide prolonged continuous exposure of the solid tumor to SN-38 when compared to the unmodified, i.e., short-acting, topoisomerase-I inhibitor compound. Due at least in part to the long-acting nature of the topoisomerase-I inhibitor compounds administered in accordance with the instant method, a correlation with clinical outcome was successfully modeled based upon levels of the illustrative MUC-1 antigen, CA27.29. As shown in FIGS. 2A, 2B and 2C, the predicted values for the tumor marker, CA27.29 (based upon the model), correlate quite well with their observed values. Thus, the PK/PD model described herein describes MUC-1 antigen tumor markers such as CA27.29 accurately, and further, allows prediction of long-acting topoisomerase-I inhibitor response from SN-38 PK data.

FIGS. 4A-4D illustrate the observed change in serum levels of CA27.29 (in percent) over time following initial dosing for individual patients in each treatment group. Notably, 93% of the patients with RECIST CR (complete responders) or PR (partial responders) exhibited declines in CA27.29. Observed maximum declines in CA27.29 by RECIST response are plotted FIG. 5.

Based upon the above, a method is provided wherein exposure of the breast cancer to SN-38 resulting from treatment of a patient diagnosed with breast cancer with a long-acting topoisomerase-I inhibitor compound correlates with the level of tumor marker in the patient (i.e., CA27.29 or CA15-3) and the efficacy of the treatment regimen, thereby allowing predictions related to the clinical outcome of treatment. In one embodiment of the method, a reduction in the level of tumor marker of at least 25% (from the reference or baseline level) by week 6 shows a positive correlation with progression-free survival in the patient of at least 4 months. See, e.g., Example 3.

Depending upon the levels of the tumor marker determined over the course of treatment, and correlation of the same with efficacy of treatment, using a model such as described herein, the dosage amount, dosing regimen, or both may be adjusted to achieve a more favorable clinical outcome for the patient.

The invention provides a method for that is useful for (among other things) treating a patient suffering from a condition that is responsive to treatment with a long-acting topoisomerase-I inhibitor compound. While administration is generally via a parenteral route, other modes of administration are also contemplated, such as pulmonary, nasal, buccal, rectal, sublingual, and transdermal. As used herein, the term "parenteral" includes subcutaneous, intravenous, intra-arterial, intraperitoneal, intracardiac, intrathecal, and intramuscular injection, as well as infusion injections.

The presently described method wherein a long-acting topoisomerase I inhibitor compound is administered to a patient may be used to treat any condition that can be remedied or prevented by this approach. Exemplary conditions are cancers, such as, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell cancer, basal cell cancer, adenocarcinoma, sweat gland cancer, sebaceous gland cancer, papillary cancer, papillary adenocarcinomas, cystadenocarcinoma, medullary cancer, bronchogenic cancer, renal cell cancer, hepatoma, bile duct cancer, choriocarcinoma, seminoma, embryonal cancer, Wilms' tumor, cervical cancer, testicular cancer, lung cancer, small cell lung cancer, bladder cancer, epithelial cancer, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma and leukemias. Most generally, the patient is one diagnosed with breast cancer.

The subject treated in accordance with the method described herein may possess any of a number of types of breast cancer, including ductal carcinoma in situ, invasive ductal carcinoma, triple negative breast cancer, inflammatory breast cancer, metastatic breast cancer, medullary carcinoma, tubular carcinoma, or mucinous carcinoma. The breast cancer may be HER2-positive. In a particular embodiment, the patient possesses metastatic breast cancer.

Subjects treated in accordance with the present method that possess breast cancer may also have received prior treatment with one or more chemotherapeutic agents. For example, the subject may possess metastatic breast cancer and have undergone prior chemotherapy with one or more of the following: a taxane drug such as docetaxel or paclitaxel; an anthracycline such as epiribuicin, doxorubicin, or mitoxantrone; capecitabine, bevacizumab, or trastuzumab.

All articles, books, patents, patent publications and other publications referenced herein are incorporated by reference in their entireties. In the event of an inconsistency between the teachings of this specification and the art incorporated by reference, the meaning of the teachings and definitions in this specification shall prevail (particularly with respect to terms used in the claims appended herein). For example, where the present application and a publication incorporated by reference defines the same term differently, the definition of the term shall be preserved within the teachings of the document from which the definition is located.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

Pentaerythritolyl-4-Arm-(PEG-1-Methylene-2 Oxo-Vinylamino Acetate linked-Irinotecan)-20K ("4-arm-PEG-gly-irino-20K") was obtained from Nektar Therapeutics (San Francisco, Calif.). Preparation of the foregoing compound is described in U.S. Pat. No. 8,263,062.

Example 1

Evaluation of Efficacy and Safety of Two Different Dosing Schedules of Pentaerythritolyl-4-Arm-(PEG-1-Methylene-2 Oxo-Vinylamino Acetate Linked-Irinotecan)-20K in Patients with Previously Treated Metastatic Breast Cancer Seventy patients were enrolled in the trial (n=35 per arm). The median patient age was 54.5 years (range, 33-83 years), ECOG performance status was zero in 40% and 1 in 60%, the median time since initial diagnosis to chemotherapeutic drug administration was 4.5 years (range, 0-19 years), and the median number of cytotoxic regimens for MBC was 2. All patients had previously received treatment with a taxane (76% docetaxel; 40% paclitaxel); 89% had received a prior anthracycline (63% epirubicin; 24% doxorubicin and one patient with mitoxantrone); and 27% of patient had received capecitabine. Fifteen (21.4%) patients had received prior bevacizumab. Among five patients with HER2-positive disease, all had received prior trastuzumab; none had received prior lapatinib.

Patients were randomized 1:1 into two treatment arms, comparing the same dose with a different dosing frequency. 4-Arm-PEG-gly-irino-20K was administered at 145 mg/m$^2$ every 14 days (q14d) or every 21 days (q21d) as an intravenous infusion over 90 minutes on day 1. Patients received treatment until disease progression or unacceptable toxicity. The drug dosage was dose-reduced by 25 mg/m$^2$ for grade 3-4 hematologic toxicity, grade 3-4 diarrhea, and other grade 2-4 non-hematologic toxicities (other than alopecia, anorexia, asthenia, and untreated nausea/vomiting). Protocol retreatment criteria required that toxicities and hematologic parameters were resolved to the following grades or levels prior to administration of the next dose: diarrhea, fully resolved; other non-hematologic toxicities, grade 1; neutrophils ≥1,500/mm$^3$; platelets ≥100,000/mm$^3$; and hemoglobin ≥9 g/dL.

Medical history was taken at screening and on day 1 of each cycle. Physical exam was performed and serum CA27.29, complete blood count with differential, and serum chemistry were analyzed at screening, on day 1 of each cycle, and at end of treatment. Coagulation parameters were analyzed at screening and on day 1 of each cycle. Radiologic exam (either computed tomography or magnetic resonance imaging, with the same method per lesion used throughout the study) occurred at screening (within 28 days of day one, cycle 1) and approximately every 6 weeks thereafter until progressive disease, start of new anticancer therapy, or end of study. Patients were contacted approximately every 3 months after the end-of-treatment visit to assess progression (in the absence of progression on study), survival, receipt of subsequent anti-cancer therapy, and resolution of toxicity.

Response was measured by RECIST version 1.0 (Therasse, P., et al., 2000, *Journal of the National Cancer Institute*, 92 (3), 205-216) and toxicities were graded according to the National Cancer Institute Common Terminology Criteria for Adverse Events (NCI-CTCAE) version 3.0.

The primary endpoint was ORR, with confirmation of all responses by a second imaging procedure at least 28 days from the initial observation of response. Secondary endpoints were PFS, overall survival (OS), 6-month and 1-year survival, and safety. Exploratory endpoints included change from baseline in CA27.29, UGT1A1 and ABCC2 polymorphism for correlation with select toxicities.

Three populations for analysis were defined: 1) intent-to-treat (ITT), 2) efficacy evaluable, and 3) safety. The ITT population was the primary population for all efficacy analyses and included all randomized patients. The efficacy evaluable population included all randomized patients with measurable disease that had at least one tumor assessment post study drug administration or had disease progression or died within 6 weeks of the first study drug administration. The safety population consisted of all patients who received at least one dose or partial dose of chemotherapeutic agent.

Summary statistics were used for continuous variables, frequency counts and percentages were used for categorical variables. Ninety-five percent confidence interval were calculated for ORR using the Exact method. Time-to-event variables were analyzed using the Kaplan-Meier method.

The chemotherapeutic agent, 4-arm-PEG-gly-irino-20K, substantially exceeded the efficacy threshold of this study, producing an objective response rate (ORR) of 28.6% when administered every 14 days or every 21 days. See Table 1 below.

TABLE 1

Efficacy Results in Patients with Metastatic Breast Cancer

| Parameter | Total |
|---|---|
| Overall Response Rate (ORR) | 29% (N = 66) |
| Progression Free Survival (PFS) | 4.6 months (5.3 months in q21d) |
| Overall Survival (OS) | 10.3 months (13.1 months q21d) |
| Overall best CA27.29 response (50% or better decline in at least one observation from baseline) | 36% (16/45) |

Example 2

CA27.29 Biomarker Measurements During Screening

An analysis dataset was created based upon the study described in Example 1. Baseline CA27.29 measurements from 48 patients with available screening values are shown in Table 2.

TABLE 2

| Baseline CA27.29 Measurements (U/mL) at Screening | | | | | |
|---|---|---|---|---|---|
| | Min | 25% Quartile | Median | 75% Quartile | Max |
| q14d (N = 26) | 13 | 38.8 | 89 | 149.5 | 3383 |
| q21d (N = 22) | 14 | 25 | 61.5 | 242 | 669 |
| Total (N = 48) | 13 | 27 | 78 | 184 | 3383 |

The analysis dataset utilized consisted of 45 patients having at least two CA27.29 measurements (pre- and post-first dose).

FIGS. 1A and 1B show the change (%) in serum CA27.29 profiles after administration of 145 mg/m² 4-arm-PEG-gly-irino-20K q14d (FIG. 1A) or q21d (FIG. 1B), where n equals the number of CA27.29 evaluable samples available after each cycle. As can be seen, the levels of the CA27.29 biomarker were found to decrease over the time course of treatment with the long-acting topoisomerase I inhibitor under both treatment regimens evaluated.

Example 3

Development of a Mathematical Model Linking the Kinetics of CA27.29 to SN-38 Exposure, Tumor Size, and RECIST A model was devised to predict a plasma SN-38 concentration-time profile for each patient based upon dosing information and a previously developed population PK model (M. A. Eldon, U. Hoch., *J. Clin Oncol*, 29: 2011 (suppl; abstr 2598)). The purpose of this model was to investigate the relationship of predicted plasma SN-38 concentrations and serum CA27.29 concentrations, and to test whether SN-38 (indirectly) inhibits the production of CA27.29.

The model is based upon the following:

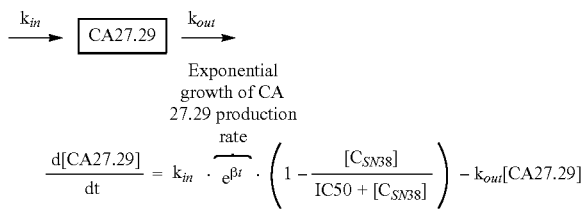

$$\frac{d[CA27.29]}{dt} = k_{in} \cdot \overbrace{e^{\beta t}}^{\text{Exponential growth of CA 27.29 production rate}} \cdot \left(1 - \frac{[C_{SN38}]}{IC50 + [C_{SN38}]}\right) - k_{out}[CA27.29]$$

where $k_{in}$ is the production rate of serum CA27.29; $k_{out}$ is the elimination rate of serum CA27.29; [CA27.29] is the serum concentration of CA27.29 (U/mL), and $[C_{SN38}]$ is the SN-38 concentration (ng/mL). The variable $e^{\beta t}$ represents the exponential growth of CA27.29 production rate, while $$\left(1 - \frac{[C_{SN38}]}{IC50 + [C_{SN38}]}\right)$$

represents the inhibitory effect.

Use of the model provided the following results. Response patterns to administration of a long-acting topoisomerase I-inhibitor were successfully modeled based upon the discovery of a correlation between SN-38 levels (derived from the administered chemotherapeutic agent, 4-arm-PEG-gly-irino-20K), and the biomarker, CA27.29. For a long-acting topoisomerase I-inhibitor such as 4-arm-PEG-gly-irino-20K or another similarly modified topoisomerase-I inhibitor, exposure of the tumor to SN-38 is greatly prolonged when compared to the unmodified drug itself. For 4-arm-PEG-gly-irino-20K, the elimination half-life is 50 days compared to 2 days for irinotecan, however, maximal concentrations are five- to ten-times less, leading to greatly reduced toxicities. Thus, due to the long-acting nature of the chemotherapeutic agent (and thus prolonged exposure to its metabolite, SN-38), a correlation with clinical outcome was successfully modeled based upon levels of CA-27.29.

The CA27.29 concentration-time profiles were well described by the model independent of response pattern. The kinetics of CA27.29 were linked to SN-38 exposure, tumor size and RECIST, to thereby provide the ability to predict response of treatment in various clinical scenarios such as changes in dose and/or schedule, the occurrence of dosing delays, and the like.

FIGS. 2A, 2B, and 2C are examples of typical CA27.29 profiles over time for individual patients treated as described in Example 1, where the observed values correspond to the circles and the individual predicted CA27.29 levels correspond to the solid line. As can be seen, the correlation is striking.

The half-life of CA27.29 decline was estimated to be 15 days, while the modeled population mean $IC_{50}$ of SN-38 was 1.6 ng/mL. In the absence of dose interruptions, the minimum plasma SN-38 concentration ($C_{min}$) at steady state reached approximately 94% and 55% of $IC_{50}$ for the q14d and q21d regimen, respectively.

Figure 3:
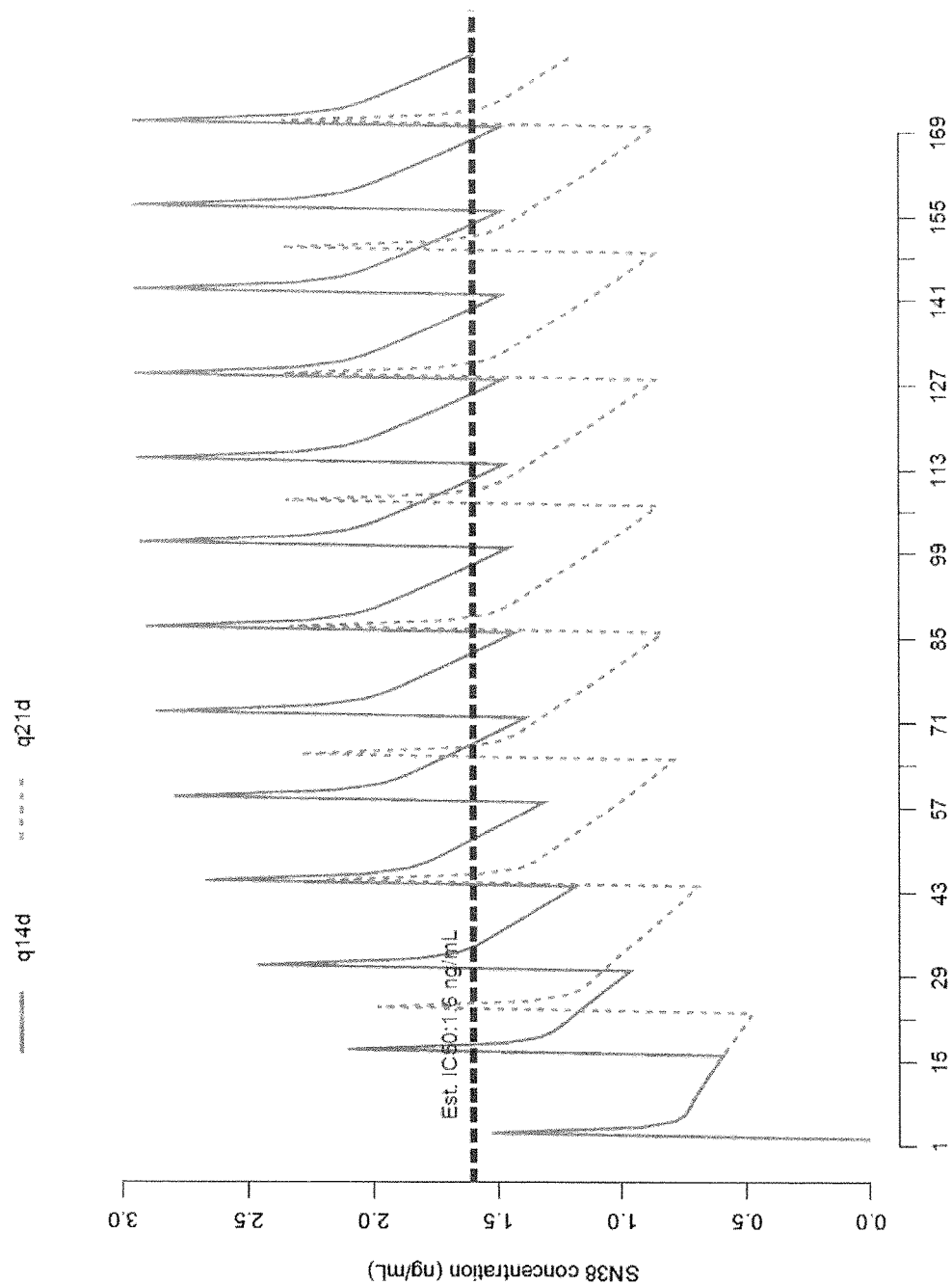
FIG. 3 is a plot with projections of SN-38 concentrations (ng/mL) over time following initial treatment for both the q14d and q21d dosing regimens based upon the model described in Example 3, where the solid line represents the q14d regimen and the dashed line represents the q21d regimen.
Figure 4A:
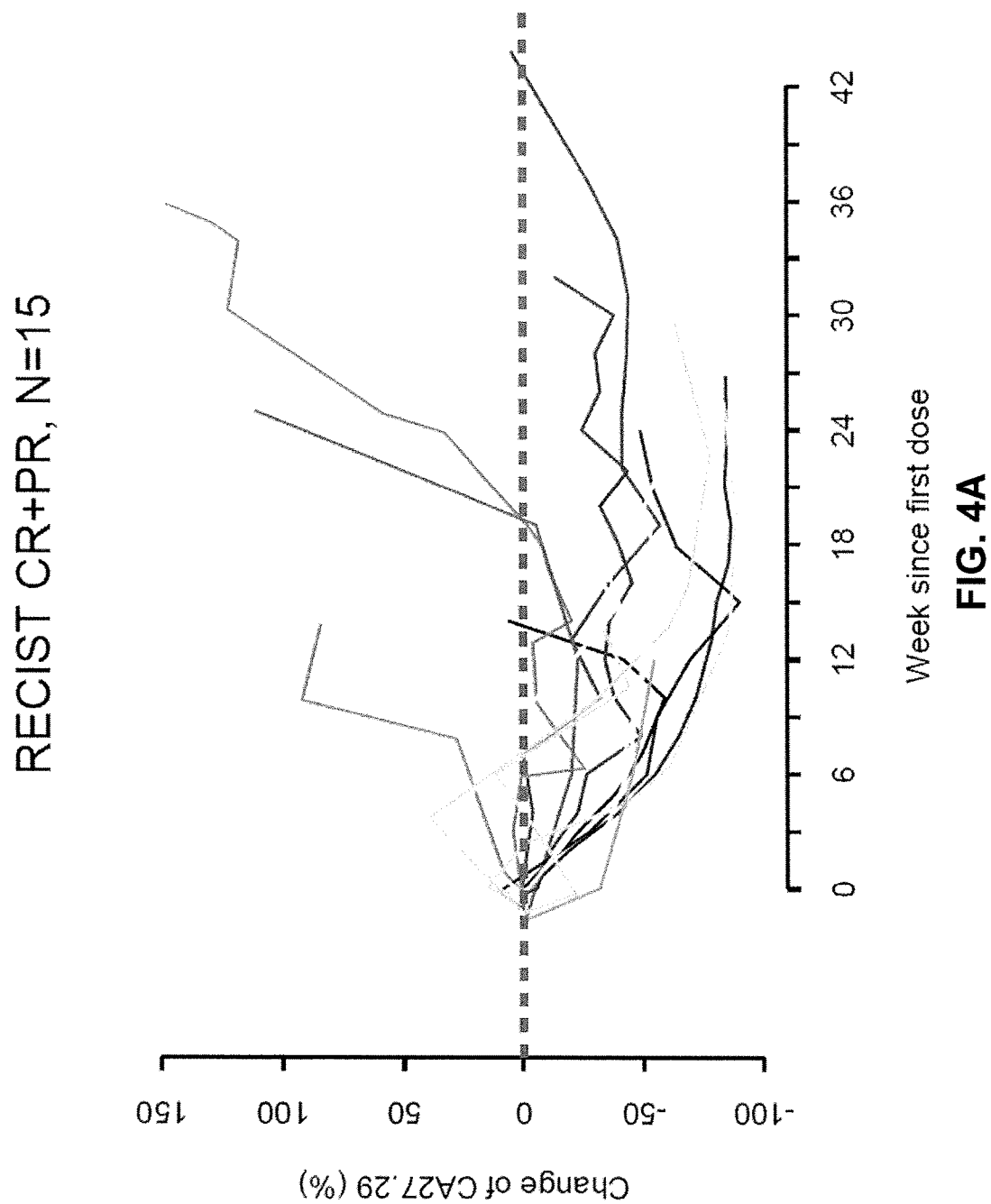
FIGS. 4A-4D are plots illustrating the observed change in serum CA27.29 in percent over time following initial dosing of an illustrative long-acting topoisomerase-I inhibitor for individual patients in each response group as described in the Examples.
Figure 4B:
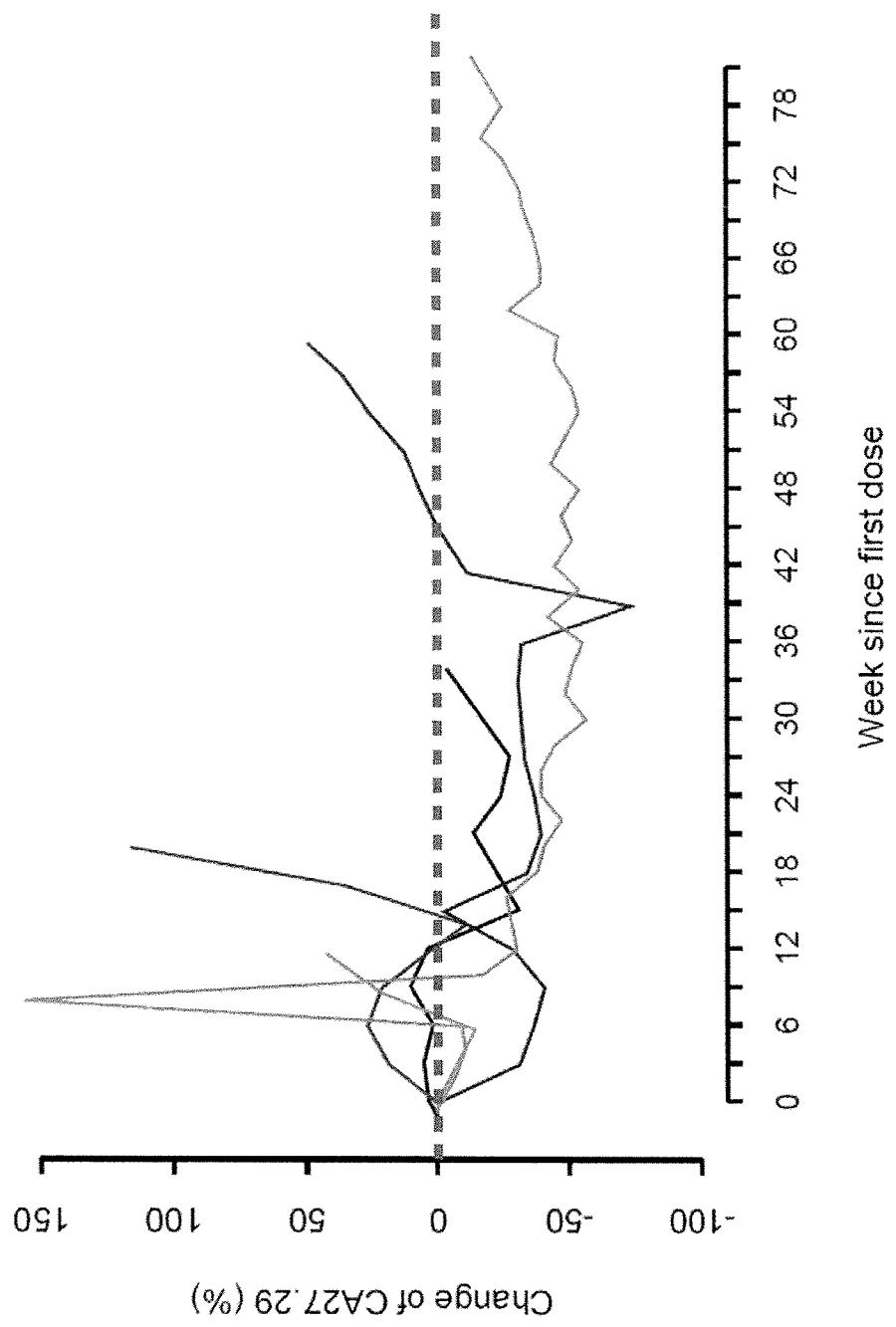
Figure 4C:
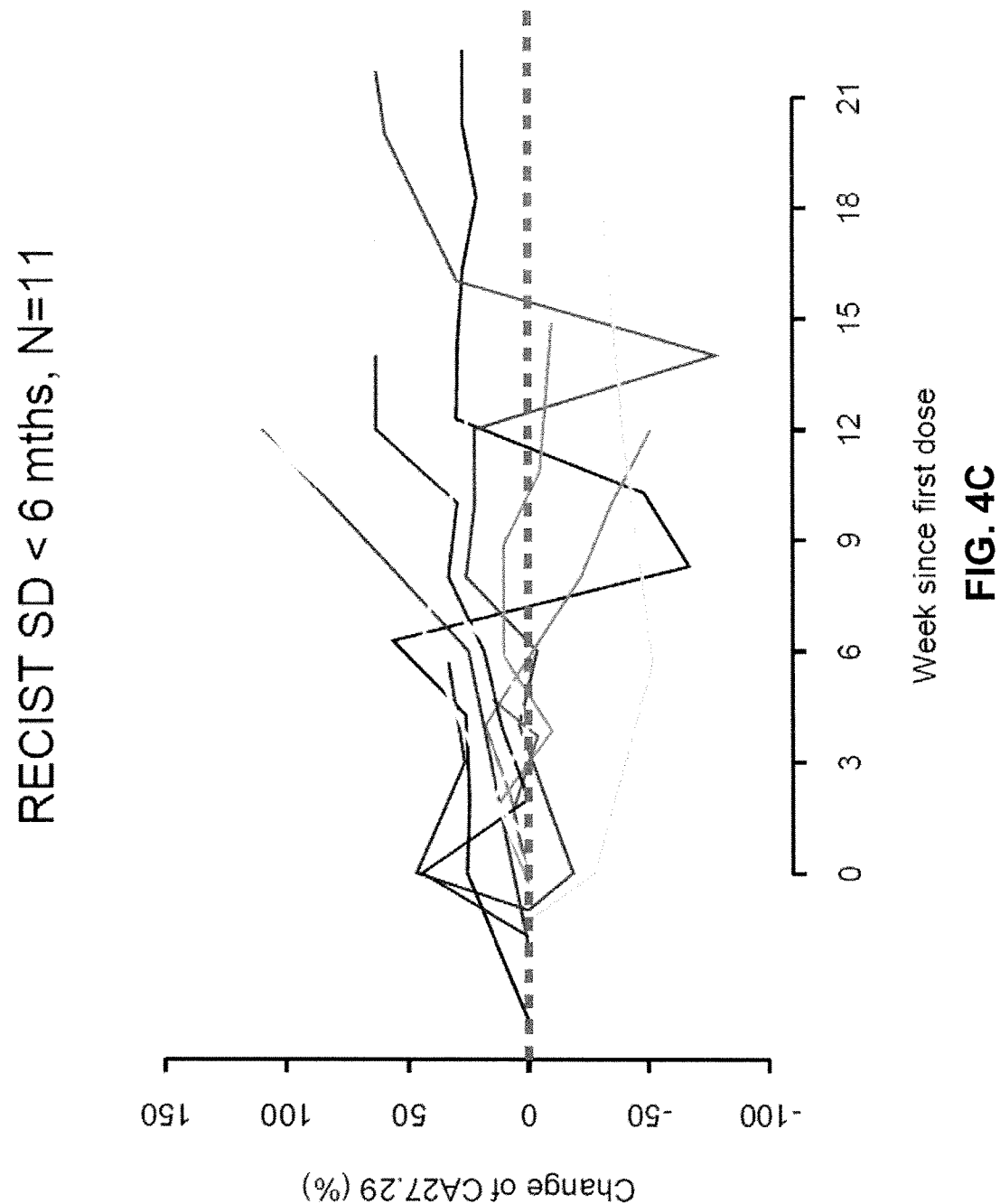
Figure 4D:
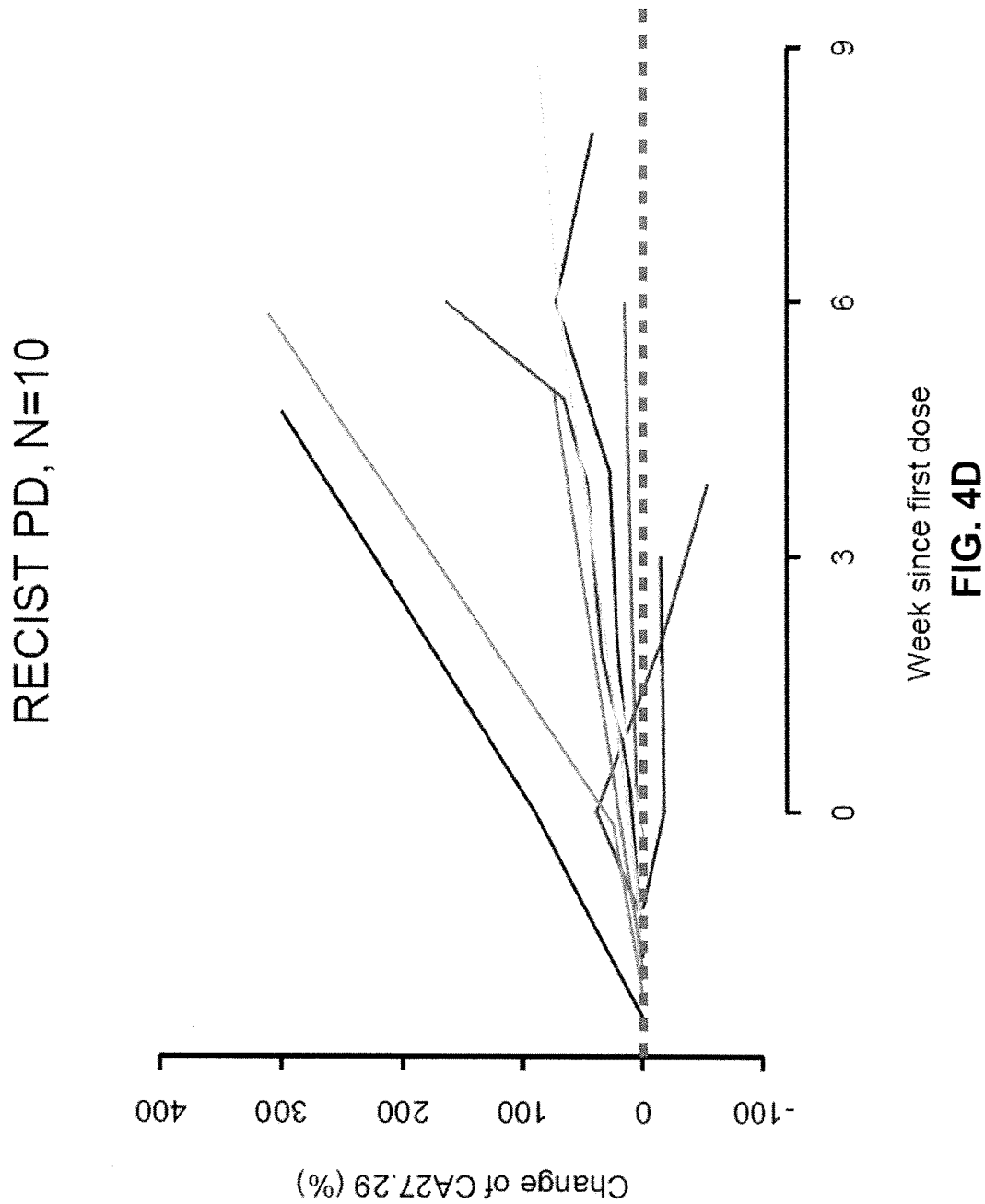

FIG. 3 is a plot with projections of SN-38 concentrations (ng/mL) over time following initial treatment for both the q14d and q21d dosing regimens, where the solid line represents the q14d regimen and the dashed line represents the q21d regimen.

Levels of CA27.29 were also evaluated for correlation with tumor size over the course of treatment. See FIGS. 4A-4D, which are plots illustrating the observed change in serum CA27.29 in percent over time following initial dosing for individual patients in each response group. Forty-one patients had pre- and post-treatment tumor measurements for correlation of CA27.29 response with tumor size. Ninety three percent (14/15) of the patients with RECIST CR (complete response) or PR (partial response) exhibited declines in CA27.29. All patients (n=5) with RECIST SD (stable disease)≥6 months also manifested declines, whereas only 55% (6/11) of the patients with SD<6 months showed a decline in CA27.29. Eighty percent (8/10) of the patients with RECIST PD (progressive disease) showed CA27.29 elevation from baseline. (See Eisenhauer, E. A., et al., *European Journal of Cancer*, 45 (2009), 228-247 for definitions related to response criteria used to determine objective tumor response for target lesions such as those used above). Larger declines in CA27.29 from baseline were associated with a better RECIST response.

Figure 5:
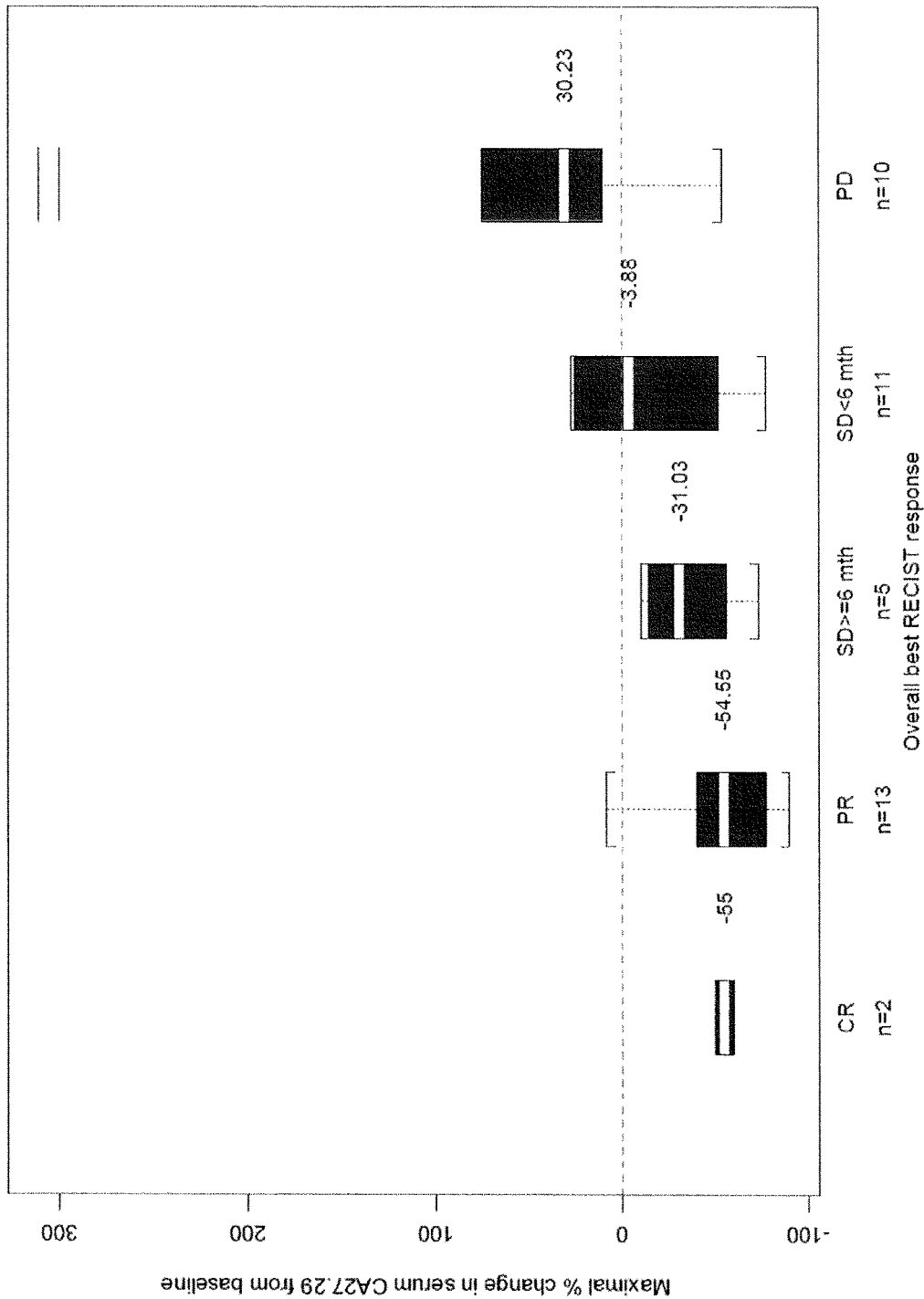
FIG. 5 is a plot of observed maximum declines in CA27.29 based upon RECIST response criteria for breast cancer patients treated with an illustrative long-acting topoisomerase-I inhibitor as described in Examples 1-3.

Observed maximum declines in CA27.29 by RECIST response are plotted in FIG. 5. For PR and CR, the median of the maximum CA27.29 decline was larger than 50%. For SD≥6 months, the median of the maximum decline in CA27.29 was also significant, but smaller, at 30%, whereas the median decline for SD<6 months was negligible. For PD, instead of decline, the median increased.

A predictor of progression-free survival (PFS) was explored based upon a minimum reduction of CA27.29 of 26% at week 6. Reduction at week 6 was chosen to avoid spurious early rises in CA27.29 that may occur during the first 4-6 weeks (based on ASCO recommendations). Among the 26 patients with ≥25% reduction in CA27.29, twelve had not progressed or discontinued treatment by week 6. The patients with ≥25% reduction by week 6 (n=12) had a median PFS of 12 months, while the patients with <25% reduction (n=4) or elevations (n=13) in CA27.29 by week 6 had a median PFS of 6 months. Simulation of 1000 patients receiving 145 mg/m² q21d projected that 46% would achieve ≥25% reduction in CA27.29 in the absence of dose reduction/interruption.

As a result of the modeling studies described, it was determined that the PK/PD model described herein accurately describes CA27.29 profiles, thereby providing a tool to predict drug response from SN-38 PK data derived from therapeutic treatment with a long-acting topoisomerase-I inhibitor such as the illustrative chemotherapeutic agent described. Moreover, changes in CA27.29 from baseline levels may constitute an early marker for treatment response to long-acting topoisomerase-I inhibitor drugs. Finally, model-predicted CA27.29 profiles after dosing with 145 mg/m² 4-arm-PEG-gly-irino-20K q21d suggests that the better-tolerated q21d schedule will produce clinical results consistent with those from both schedules used in the phase 2 study.

What is claimed is:

1. A method for treating and assessing response to treatment with a long-acting topoisomerase-I inhibitor selected from SN-38 and irinotecan in a subject having metastatic breast cancer, the method comprising:
   (i) determining the level of a tumor marker in a bodily fluid sample of the subject selected from blood, plasma, and serum to provide a reference level of the tumor marker, where the tumor marker is CA27.29;
   (ii) treating said subject over a duration of time of at least 2 weeks by administering a dosage amount of the long-acting topoisomerase-I inhibitor on a given dosing schedule, wherein the long-acting topoisomerase-I inhibitor is pentaerythritolyl-4-arm-(polyethyleneglycol-1-methylene-2 oxo-vinylamino acetate-linked irinotecan), or a pharmaceutically acceptable salt thereof, or has a structure:

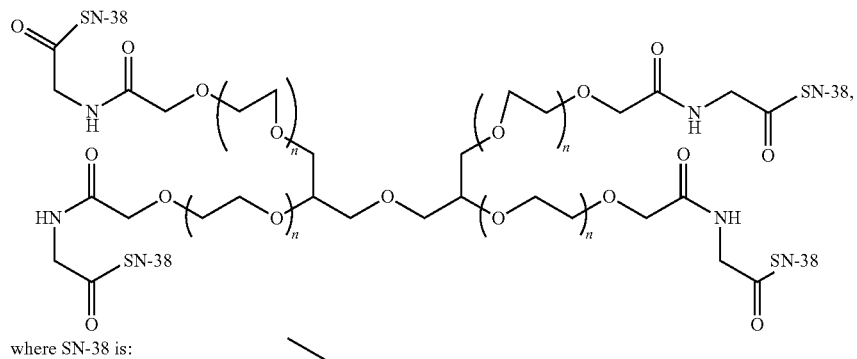

where SN-38 is:

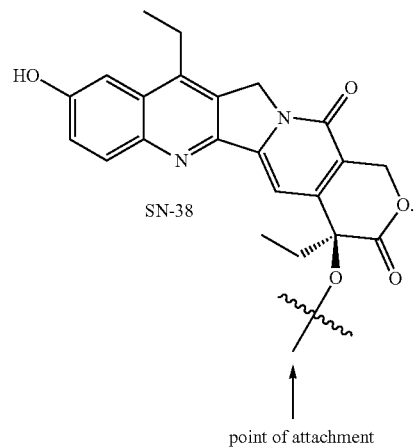

or a pharmaceutically acceptable salt thereof;
   (iii) determining the level of the tumor marker in a bodily fluid sample obtained from the subject following treatment of the subject according to step (ii), and within 6 weeks following initial administration of the long-acting topoisomerase-I inhibitor, wherein the bodily fluid is the same as in step (i); and
   (iv) correlating the level of the tumor marker in step (iii) with response of the metastatic breast cancer to treatment with the long-acting topoisomerase-I inhibitor, wherein, in the event of a level of the tumor marker in step (iii) that is either unchanged or reduced from the reference level in step (i), a positive response to treatment is determined, and, in the event of a level of the tumor marker in step (iii) that is increased from the reference level in step (i), a negative response to treatment is determined;
   where, in the event of determining a negative response to treatment in step (iv), either the dosage amount or dosing schedule in step (ii), or both, are altered.

2. The method of claim 1, wherein in step (i), the level of the tumor marker is determined prior to treatment with the long-acting topoisomerase-I inhibitor.

3. The method of claim 1, wherein the bodily fluid sample in steps (i) and (iii) is serum.

4. The method of claim 1, wherein the reference level of the tumor marker in step (i) is elevated over normal baseline levels.

5. The method of claim 4, wherein the tumor marker is CA27.29 and the reference level of CA27.29 is greater than 38 U/ml.

6. The method of claim 1, wherein the duration of treatment is at least 3 weeks.

7. The method of claim 6, wherein the duration of treatment is at least 6 weeks.

8. The method of claim 7, wherein the duration of treatment is at least 12 weeks.

9. The method of claim 1, wherein the level of the tumor marker is determined by an immunoassay.

10. The method of claim 1, wherein a reduction in the level of the tumor marker of at least 25% by week 6 shows a positive correlation with progression-free survival in the subject of at least 4 months.

11. The method of claim 1, wherein step (iii) is optionally repeated, either following additional treatment with the long-acting topoisomerase inhibitor I or following the cessation of treatment.

12. The method of claim 1, wherein the subject has failed to respond to prior taxane-based treatment for the metastatic breast cancer.

13. The method of claim 1, wherein the long-acting topoisomerase-I inhibitor is pentaerythritolyl-4-arm-(polyethyleneglycol-1-methylene-2 oxo-vinylamino acetate-linked-irinotecan), or a pharmaceutically acceptable salt thereof.

14. The method of claim 13, wherein step (ii), the long-acting topoisomerase-I inhibitor is administered every 14 days.

15. The method of claim 13, wherein step (ii), the long-acting topoisomerase-I inhibitor is administered every 21 days.

16. The method of claim 13, wherein a reduction in the level of CA27.29 of greater than or equal to 25% at week 6 is indicative of a median progression free survival of the subject of 12 months.

17. The method of claim 13, wherein the exposure of the metastatic breast cancer to SN-38 resulting from the treating step correlates with the level of CA27.29 in the subject and efficacy of the treatment.

* * * * *